(12) United States Patent
Devesa Giner et al.

(10) Patent No.: US 11,274,073 B2
(45) Date of Patent: Mar. 15, 2022

(54) TRPV1 MODULATOR COMPOUNDS

(71) Applicant: ANTALGENICS, S.L., Elche (ES)

(72) Inventors: Isabel Devesa Giner, Elche (ES); Armando Genazzani, Novara (IT); Tracey Pirali, Novara (IT); Asia Fernandez Carvajal, Elche (ES); Antonio Vicente Ferrer Montiel, Elche (ES)

(73) Assignee: ANTALGENICS, S.L., Elche (ES)

( * ) Notice: Subject to any disclaimer, the term of this patent is extended or adjusted under 35 U.S.C. 154(b) by 179 days.

(21) Appl. No.: 16/608,841

(22) PCT Filed: May 10, 2018

(86) PCT No.: PCT/EP2018/062169
§ 371 (c)(1),
(2) Date: Oct. 27, 2019

(87) PCT Pub. No.: WO2018/206742
PCT Pub. Date: Nov. 15, 2018

(65) Prior Publication Data
US 2020/0199063 A1    Jun. 25, 2020

(30) Foreign Application Priority Data
May 11, 2017  (EP) .................................... 17382266

(51) Int. Cl.
*C07C 235/08* (2006.01)
*C07C 231/06* (2006.01)
(Continued)

(52) U.S. Cl.
CPC .......... *C07C 235/08* (2013.01); *C07C 231/06* (2013.01); *A61P 17/04* (2018.01); *A61P 29/00* (2018.01)

(58) Field of Classification Search
CPC ..... C07C 235/08; C07C 231/06; A61K 31/23; A61K 31/231; A61K 31/232; A61P 17/00;
(Continued)

(56) References Cited

U.S. PATENT DOCUMENTS
3,689,557 A    9/1972   McCaully et al.

FOREIGN PATENT DOCUMENTS
WO   WO2015/160842 A1   10/2015

OTHER PUBLICATIONS
Database Registry [Online] Chemical Abstracts Service, Columbus, Ohio, US; Apr. 9, 2003 (Apr. 9, 2003), retrieved from STN Database accession No. 502452-07-5.*
(Continued)

*Primary Examiner* — Deborah D Carr
(74) *Attorney, Agent, or Firm* — Squire Patton Boggs (US) LLP

(57) ABSTRACT

The present invention relates to TRPV1 modulator compounds of formula (I) or their pharmaceutically, veterinary or cosmetically acceptable salts, or their stereoisomers or mixtures thereof, wherein m is an integer selected from 1 to 3; $R^1$, $R^2$, $R^6$ and $R^{6'}$ are independently selected from H, $(C_1-C_8)$alkyl, unsaturated $(C_2-C_8)$hydrocarbon, and $(C_3-C_6)$ cycloalkyl, being these groups optionally substituted; $R^3$ is hydrogen or halogen; $R^4$ is selected from H, $(C_1-C_8)$alkyl, unsaturated $(C_2-C_8)$hydrocarbon, $(C_3-C_6)$cycloalkyl, $(C_6-C_{12})$aryl, and $(C_5-C_{12})$heteroaryl, being these groups optionally substituted; and $R^5$ is selected from $(C_3-C_{28})$alkyl, unsaturated $(C_3-C_{28})$hydrocarbon, $(C_6-C_{12})$aryl, and $(C_5-C_{12})$heteroaryl, being these groups optionally substituted. It also relates to a process for their preparation, to pharma-
(Continued)

ceutical, veterinary or cosmetic compositions containing them, and to their pharmaceutical, veterinary and cosmetic applications.

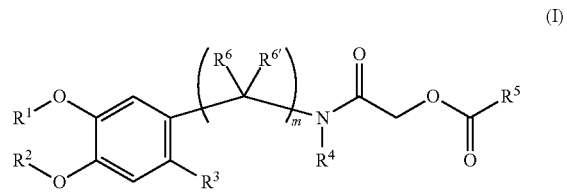

(I)

16 Claims, 3 Drawing Sheets

(51) Int. Cl.
*A61P 29/00* (2006.01)
*A61P 17/04* (2006.01)
(58) Field of Classification Search
CPC .......... A61P 25/00; A61P 35/00; A61P 29/00; A61P 17/04
USPC ........................................................ 514/627
See application file for complete search history.

(56) References Cited

OTHER PUBLICATIONS

Database Registry [Online] Chemical Abstracts Service, Columbus, Ohio, US; Dec. 3, 2002 (Dec. 3, 2002), retrieved from STN Database accession No. 474908-17-3.*
Database Registry [Online] Chemical Abstracts Service, Columbus, Ohio, US; Dec. 3, 2002 (Dec. 3, 2002), retrieved from STN Database accession No. 474908-01-5.*
Database Registry [Online] Chemical Abstracts Service, Columbus, Ohio, US; Jul. 5, 2015 (Jul. 5, 2015), retrieved from STN Database accession No. 1794910-30-7.*
Database Registry [Online] Chemical Abstracts Service, Columbus, Ohio, US; Aug. 21, 2011 (Aug. 21, 2011), retrieved from STN Database accession No. 1320523-21-4.*
Database Registry [Online] Chemical Abstracts Service, Columbus, Ohio, US; May 29, 2011 (May 29, 2011), retrieved from STN Database accession No. 1302213-65-5.*
Database Registry [Online] Chemical Abstracts Service, Columbus, Ohio, US; May 22, 2011 (May 22, 2011), retrieved from STN Database accession No. 1298494-89-9.*
Database Registry [Online] Chemical Abstracts Service, Columbus, Ohio, US; May 1, 2011 (May 1, 2011), retrieved from STN Database accession No. 1288316-95-9.*

Bode, A. M. et al. "The two faces of capsaicin" Cancer Res. 2011, 71(8), 2809-2814.
Li S. et al, "TRPV1 antagonist AMG9810 promotes mouse skin tumorigenesis through EGFR/Akt signalling", Carcinogenesis 2011, 32 (5), pp. 779-785.
Collado et al, "Metalation vs Nucleophilic Addition in the Reactions of N-Phenethylimides with Organolithium Reagents. Ready Access to Isoquinoline Derivatives via N-Acyliminium Ions and Parham-Type Cyclizations", J. Org. Chem. 1997, 62, 2080-2092.
Collado et al., "Parham-type Cyclization and Nucleophilic Addition-N-Acyliminium ion Cyclization Sequences for the Construction of the Isoquinoline Nucleus", Tetrahedron Letters 1996, vol. 37, No. 34, pp. 6193-6196.
Green et al., Protective Groups in Organic Chemistry, Wiley, 3rd ed. 1999, Chapter 2, pp. 17-200.
Weber et al., "Expression and functionality of TRPV1 in breast cancer cells", Breast Cancer. 2016 13, 8, pp. 243-252.
Moran et al., "Transient receptor potential channels as therapeutic targets", Nat. Rev. Drug Discov. 2011, 10(8), pp. 601-620.
Garcia-Martinez et al., "Design and characterization of a noncompetitive antagonist of the transient receptor potential vanilloid subunit 1 channel with in vivo analgesic and anti-inflammatory activity", J. Pain 2006, 7(10), pp. 735-746.
In Kueper et al., "Inhibition of TRPV1 for the treatment of sensitive skin", Exp. Dermatol. 2010, 19(11), pp. 980-986.
Lee et al, "The role of TRPV1 channel in aged human skin", Journal of Dermatological Science 2012, 65, pp. 81-85.
Toth et al., "TRP channels in the skin", Br. J. Pharmacol. 2014, 171(10), pp. 2568-2581.
Schaible, "Nociceptive neurons detect cytokines in arthritis", Arthritis Res Ther. 2014, 16(5), 470.
Toth et al, "Transient receptor potential vanilloid-1 signaling as a regulator of human sebocyte biology" J Invest Dermatol. 2009, 129(2), pp. 329-339.
Yun et al., "Antipruritic effects of TRPV1 antagonist in murine atopic dermatitis and itching models", J Invest Dermatol. 2011, 131(7), pp. 1576-1579.
Klopman et al: "Quantitative structure-agonist activity relationship of capsaicin analogues", Journal of Computer-aided Molecular Des, 1995, vol. 9, No. 3, pp. 283-294.
Chemical Abstracts Service—Database accession No. 502452-07-5.
Chemical Abstracts Service—Database accession No. 474908-17-3.
Chemical Abstracts Service—Database accession No. 474908-01-5.
Chemical Abstracts Service—Database accession No. 1794910-30-7.
Chemical Abstracts Service—Database accession No. 1320523-21-4.
Chemical Abstracts Service—Database accession No. 1302213-65-5.
Chemical Abstracts Service—Database accession No. 1298494-89-9.
Chemical Abstracts Service—Database accession No. 1288316-95-9.

* cited by examiner

TRPV1 MODULATOR COMPOUNDS

CROSS-REFERENCE TO RELATED APPLICATIONS

This application is a U.S. national stage application, filed under 35 U.S.C. 371, of International Patent Application No. PCT/EP2018/062169, filed on May 10, 2018, claims the priority benefit of European Patent Application EP17382266.9 filed on May 11, 2017, all of which are incorporated herein by reference in their entirety.

TECHNICAL FIELD

The present invention relates to the field of pharmacy, veterinary and cosmetics. More particularly, it relates to novel compounds, which are modulators of vanilloid receptor 1 (TRPV1). It also relates to a process for their preparation, to pharmaceutical, veterinary or cosmetic compositions containing them, and to their pharmaceutical, veterinary and cosmetic uses.

BACKGROUND ART

Nociception is the sensory nervous system's response to certain harmful or potentially harmful stimuli including mechanical, thermal and chemical stimuli. Nociceptors transmit this information to the central nervous system leading to the sensation of pain. Most nociceptors are cation channels including transient receptor potential (TRP) channels.

The TRP family includes more than 30 cation channels, the majority of which are permeable to divalent and monovalent cations, including $Ca^{2+}$, $Na^+$, and $Mg^{2+}$. The transient receptor potential vanilloid 1 (TRPV1) receptor, also known as capsaicin receptor and vanilloid receptor 1 (VR1), is a nonselective cation channel which belongs to this family of ion channels. The function of TRPV1 is the detection and regulation of body temperature. In addition, it provides a sensation of scalding heat and pain (nociception).

TRPV1 is present in the pain sensory nerve, as well as in other tissues such as brain, kidney, bronchial epithelial cells, and epidermal keratinocytes. It plays a significant role in the pain transduction pathway and has a well-defined pro-inflammatory role in a variety of diseases and injury states.

There are two mechanisms of inhibition of the TRPV1 receptor: i) desensitization of the receptor produced by TRPV1 agonists, and ii) inhibition of the receptor produced by TRPV1 antagonists. Therefore, both agonists and antagonists are useful in combating conditions mediated by the inhibition of the TRPV1 receptor.

In the case of TRPV1 agonists, it is believed that when TRPV1 is continuously activated through prolonged exposure to the agonist, excessive calcium enters the nerve fiber, initiating processes that result in long-term yet reversible impairment of nociceptor function and thus provide relief from pain. Capsaicin or the capsaicin analogue resiniferatoxin (RTX) are known TRPV1 agonists. Capsaicin acts as an anti-inflammatory agent, antipruritic, anti-psoriatic and anti-itch agent and has been reported to cause apoptosis and/or inhibit proliferation of malignant cancer cells. However, the application of capsaicin as a therapeutic agent is difficult due to its irritating effect and burning sensation, which causes patients to stop treatment in advance.

Furthermore, in long term treatments, it is known that the accumulation of capsaicin in the skin can cause cancer (Cancer Res. 2011, 71(8), pp. 2809-2814).

On the other hand, TRPV1 antagonists, such as AMG9810 ([(E)-3-(4-t-butylphenyl)-N-(2,3-dihydro-benzo[b][1,4] dioxin-6-yl)acrylamide]), block TRPV1 activity, thus reducing pain. TRPV1 antagonists have been disclosed as being effective in patients having migraine, chronic intractable pain secondary to cancer, AIDS or diabetes. Moreover, recent data indicate that TRPV1 antagonists could also be useful in treating disorders other than pain, such as urinary urge incontinence, chronic cough and irritable bowel syndrome. However, similarly to capsaicin, it has been reported that TRPV1 antagonist AMG9810 promotes mouse skin tumorigenesis (Carcinogenesis 2011, 32 (5), pp. 779-785).

Furthermore, it has been suggested that TRPV1 inhibitory compounds may be good candidates to treat and prevent skin aging process, including heat-induced skin aging, UV-induced photoaging, and intrinsic skin aging, as well as other skin conditions such as sensitive skin, itch (pruritus), and rosacea.

Although in recent years a lot of effort has been made in the research of TRPV1 modulators, only a small number of drugs have reached advanced clinical development. Therefore, there is still a need of developing compounds which show improved activity in conditions and/or diseases mediated by TRPV1 and overcomes the problems of the prior art compounds.

SUMMARY OF INVENTION

Inventors have found new compounds having a 3,4-dioxy substituted phenyl moiety linked to a substituted (acetyloxy) acetamidoalkyl moiety that are modulators of TRPV1. As demonstrated by the examples, the compounds of the invention include both TRPV1 agonists and TRPV1 antagonists. Further, in in vivo models of inflammation, the compounds of the invention did not show any toxicity and showed significant antinociceptive effects. Therefore, these compounds could be useful for the treatment and/or prevention of conditions and/or diseases mediated by the inhibition of TRPV1.

An advantage of the compounds of the invention is that after performing their effect they have the ability to be metabolized thanks to the ester bond, susceptible to be hydrolyzed by esterases, and thus be subsequently eliminated. Therefore, these compounds are not accumulated in the body and are particularly useful for the treatment or prevention or chronic diseases requiring periodic administration of the active compounds. Thus, the compounds of the invention both not only show an improved activity but also avoid the side effects found in the prior art compounds that have been developed so far such as the irritant effect of capsaicin or the carcinogenic activity due to its accumulation in the skin.

Therefore, a first aspect of the invention relates to a compound of formula (I), or a pharmaceutically, veterinary or cosmetically acceptable salt thereof, or any stereoisomer or mixtures thereof, either of the compound of formula (I) or of any of its pharmaceutically, veterinary or cosmetically acceptable salts

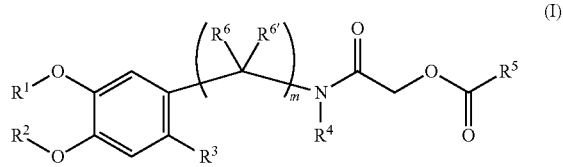

wherein m is an integer selected from 1 to 3;

$R^1$, $R^2$, $R^6$ and $R^{6'}$ are independently selected from the group consisting of H, $(C_1-C_8)$alkyl, unsaturated $(C_2-C_8)$ hydrocarbon, and $(C_3-C_6)$cycloalkyl;

wherein $(C_1-C_8)$alkyl, unsaturated $(C_2-C_8)$hydrocarbon, and $(C_3-C_6)$cycloalkyl are optionally substituted with one or more substituents selected from the group consisting of halogen, —COOH, —OH, —$NH_2$, —$COOR_6$, —$NO_2$, —$CF_3$, —$OCF_3$, —CN, —$OR_6$, —$CONH_2$, —$CONHR_6$, —$CONR_6R_7$, —$NHR_6$, —$NR_6R_7$, —$NHCOR_6$, —$NHSO_2R_6$, and —$SO_2NHR_6$;

$R^3$ is hydrogen or halogen;

$R^4$ is selected from the group consisting of H, $(C_1-C_8)$ alkyl, unsaturated $(C_2-C_8)$hydro-carbon, $(C_3-C_6)$cycloalkyl, $(C_6-C_{12})$aryl and $(C_5-C_{12})$heteroaryl;

wherein $(C_1-C_8)$alkyl, unsaturated $(C_2-C_8)$hydrocarbon, $(C_3-C_6)$cycloalkyl, $(C_6-C_{12})$aryl and $(C_5-C_{12})$heteroaryl are optionally substituted with one or more substituents selected from the group consisting of halogen, —COOH, —OH, —$NH_2$, —$COOR_6$, —$NO_2$, —$CFS$, —$OCF_3$, —CN, —$OR_6$, —$CONH_2$, —$CONHR_6$, —$CONR_6R_7$, —$NHR_6$, —$NR_6R_7$, —$NHCOR_6$, —$NHSO_2R_6$, and —$SO_2NHR_6$;

$R^5$ is $(C_3-C_{28})$alkyl, unsaturated $(C_3-C_{28})$hydrocarbon, $(C_6-C_{12})$aryl and $(C_5-C_{12})$heteroaryl; wherein $(C_1-C_8)$alkyl, unsaturated $(C_2-C_8)$hydrocarbon, $(C_6-C_{12})$aryl and $(C_5-C_{12})$ heteroaryl are optionally substituted with one or more substituents selected from the group consisting of halogen, —COOH, —OH, —$NH_2$, —$COOR_6$, —$NO_2$, —$CF_3$, —$OCF_3$, —CN, —$OR_6$, —$CONH_2$, —$CONHR_6$, —$CONR_6R_7$, —$NHR_6$, —$NR_6R_7$, —$NHCOR_6$, —$NHSO_2R_6$, and —$SO_2NHR_6$;

with the proviso that the compound of formula (I) is other than:

(3,4-dimethoxyphenethylcarbamoyl)methyl but-2-enoate; (3,4-dimethoxyphenethyl-carbamoyl)methyl 4-methylpentanoate; (3,4-dimethoxybenzylcarbamoyl)methyl 3,3-dimethylbutanoate; (3,4-dimethoxyphenethylcarbamoyl)methyl 3,3-dimethylbutanoate; (3,4-dimethoxyphenethylcarbamoyl)methyl 3-methylbut-2-enoate; (3,4-dimethoxy-benzyl-carbamoyl)methyl 4-methylpentanoate; (3,4-dimethoxybenzylcarbamoyl)-methyl 3-methylbut-2-enoate; (2E,4E)-(3,4-dimethoxybenzylcarbamoyl)methyl hexa-2,4-dienoate; (3,4-dimethoxybenzylcarbamoyl)methyl butyrate; (3,4-dimethoxyphenethylcarbamoyl)-methyl butyrate; (3,4-dimethoxyphenethylcarbamoyl)methyl hexa-2,4-dienoate; (3,4-dimethoxyphenethylcarbamoyl)methyl 2-ethylbutanoate; (3,4-dimethoxybenzyl-carbamoyl)methyl but-2-enoate; (3,4-dimethoxybenzylcarbamoyl)methyl but-3-enoate; (3,4-dimethoxybenzylcarbamoyl)methyl but-3-enoate; (3,4-dimethoxy-benzyl-carbamoyl)methyl undec-10-enoate; (3,4-dimethoxybenzylcarbamoyl)methyl 2-methylpentanoate; and 2-(3,4-dimethoxyphenethylcarbamoyl)propan-2-ylpentanoate.

Another aspect of the present invention relates to a process for the preparation of the compounds of formula (I) as defined above, which comprises:

a) reacting a compound of formula (II) with a compound of formula (III)

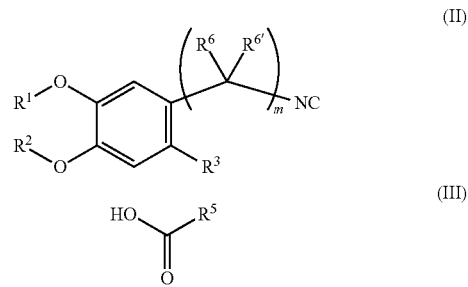

wherein $R^1$, $R^2$, $R^3$, $R^5$, $R^6$, $R^{6'}$ and m are as defined above; in the presence of formaldehyde to yield a compound of formula (I);

b) optionally converting, in one or a plurality of steps, the compound of formula (I) thus obtained into another compound of formula (I); and c) optionally reacting the compound of formula (I) obtained in any of the steps a) or b) with a base or with an acid to give the corresponding salt.

The compounds of the invention can be formulated in different types of compositions. Thus, another aspect of the invention relates to a pharmaceutical, veterinary or cosmetic composition, which comprises an effective amount of a compound of formula (I) as defined above, including (3,4-dimethoxyphenethylcarbamoyl)methyl but-2-enoate; (3,4-dimethoxyphenethylcarbamoyl)methyl 4-methylpentanoate; (3,4-dimethoxybenzyl-carbamoyl)methyl 3,3-dimethylbutanoate; (3,4-dimethoxyphenethylcarbamoyl)methyl 3,3-dimethylbutanoate; (3,4-dimethoxyphenethylcarbamoyl) methyl 3-methylbut-2-enoate; (3,4-dimethoxybenzylcarbamoyl)methyl 4-methylpentanoate; (3,4-dimethoxybenzyl-carbamoyl)-methyl 3-methylbut-2-enoate; (2E,4E)-(3,4-dimethoxybenzylcarbamoyl)methyl hexa-2,4-dienoate; (3,4-dimethoxybenzylcarbamoyl)methyl butyrate; (3,4-dimethoxyphenethylcarbamoyl)-methyl butyrate; (3,4-dimethoxyphenethylcarbamoyl)methyl hexa-2,4-dienoate; (3,4-dimethoxyphenethylcarbamoyl)methyl 2-ethylbutanoate; (3,4-dimethoxybenzyl-carbamoyl)methyl but-2-enoate; (3,4-dimethoxybenzylcarbamoyl)methyl but-3-enoate; (3,4-dimethoxybenzylcarbamoyl)methyl but-3-enoate; (3,4-dimethoxy-benzylcarbamoyl)methyl undec-10-enoate; (3,4-dimethoxybenzylcarbamoyl)methyl 2-methylpentanoate; and 2-(3,4-dimethoxyphenethylcarbamoyl)-propan-2-ylpentanoate; together with one or more pharmaceutically, veterinary or cosmetically acceptable excipients or carriers.

As mentioned above, the compounds of the invention are useful in the treatment and/or prevention of conditions or diseases mediated by the inhibition of TRPV1. Thus, another aspect of the invention relates to a compound of formula (I) as defined above, including (3,4-dimethoxyphenethylcarbamoyl)methyl but-2-enoate; (3,4-dimethoxy-phenethylcarbamoyl)methyl 4-methylpentanoate; (3,4-dimethoxybenzylcarbamoyl)methyl 3,3-dimethylbutanoate; (3,4-dimethoxyphenethylcarbamoyl)methyl 3,3-dimethylbutanoate; (3,4-dimethoxyphenethylcarbamoyl) methyl 3-methylbut-2-enoate; (3,4-dimethoxybenzylcarbamoyl)methyl 4-methylpentanoate; (3,4-dimethoxybenzylcarbamoyl)-methyl 3-methylbut-2-enoate; (2E,4E)-(3,4-dimethoxybenzylcarbamoyl)methyl hexa-2,4-dienoate; (3,4-dimethoxybenzylcarbamoyl)methyl butyrate; (3,4-dimethoxyphenethylcarbamoyl)-methyl butyrate; (3,4-dimethoxyphenethylcarbamoyl)methyl hexa-2,4-dienoate;

(3,4-dimethoxyphenethylcarbamoyl)methyl 2-ethylbutanoate; (3,4-dimethoxybenzyl-carbamoyl)methyl but-2-enoate; (3,4-dimethoxybenzylcarbamoyl)methyl but-3-enoate; (3,4-dimethoxybenzylcarbamoyl)methyl but-3-enoate; (3,4-dimethoxybenzyl-carbamoyl)methyl undec-10-enoate; (3,4-dimethoxybenzylcarbamoyl)methyl 2-methylpentanoate; and 2-(3,4-dimethoxyphenethyl-carbamoyl)propan-2-ylpentanoate; for use in the treatment and/or prevention of conditions or diseases mediated by the inhibition of TRPV1.

DETAILED DESCRIPTION OF THE INVENTION

Figure 1:
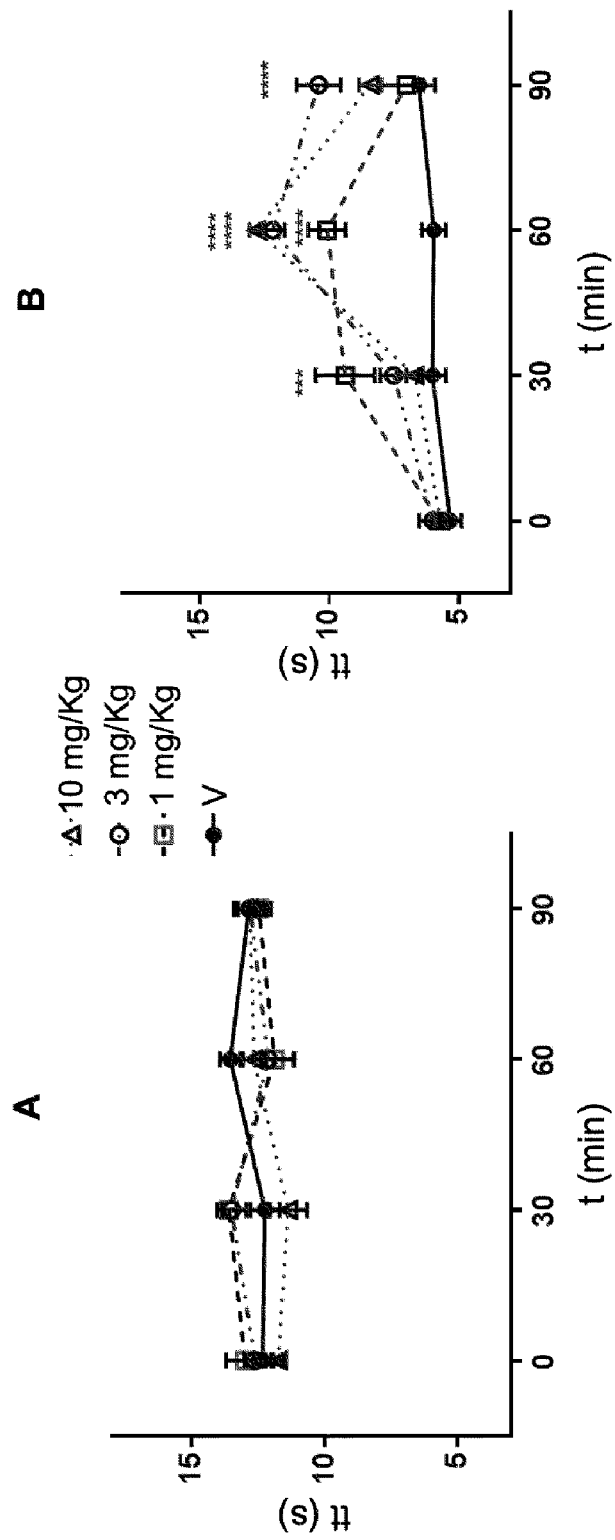
FIG. 1 shows the effect of a compound of the invention (Ex-37) by intravenous administration in the CFA-induced paw inflammation model in comparison to vehicle (V) in the left (A) and in the right hind paw (B). The diagram shows the paw withdrawal latencies (tt) over time (t) in response to thermal stimulation (n=6 mice/group). Data are given as mean±SEM n=6. 2-way ANOVA with Bonferroni post hoc test. *$P<0.05$; $P<0.01$, *$P<0.001$, ***$P<0.0001$.

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

"Protective group" (PG) refers to a group of atoms that when attached to a reactive group in a molecule masks, reduces or prevents that reactivity.

The expression "substituted with one or more" means that a group can be substituted with one or more, preferably with 1, 2, 3 or 4 substituents, provided that this group has enough positions susceptible of being substituted.

For the purposes of the invention, room temperature is 20-25° C.

The term "$(C_p-C_n)$alkyl" refers to a saturated branched or linear hydrocarbon chain which contains from p to n carbon atoms and only single bonds. Non limiting examples of alkyl groups include methyl, ethyl, propyl, butyl, isopropyl, 1-methylpropyl, 2-methylpropyl, pentyl, hexyl, heptyl, octyl, nonyl, decyl, undecyl, dodecyl, pentadecyl, and the like.

The term "unsaturated $(C_p-C_n)$hydrocarbon" refers to an unsaturated branched or linear hydrocarbon chain which contains from p to n carbon atoms and one or more double bonds and/or one or more triple bonds. Thus, the term "unsaturated $(C_p-C_n)$hydrocarbon" encompasses $(C_p-C_n)$ alkenyl and $(C_p-C_n)$alkynyl, wherein the term "$(C_p-C_n)$ alkenyl" refers to an unsaturated branched or linear hydrocarbon chain which comprises from p to n carbon atoms and at least one or more double bonds; and the term "$(C_p-C_n)$ alkynyl" refers to an unsaturated branched or linear hydrocarbon chain which comprises from p to n carbon atoms and at least one or more triple bonds. Non limiting examples of unsaturated $(C_p-C_n)$hydrocarbon groups include vinyl, propenyl, allyl, oleyl, ethynyl, propyn-1-yl, propyn-2-yl, but-1-en-3-ynyl, hexa-1,3-dien-5-ynyl, and the like.

The term halogen means fluoro, chloro, bromo or iodo.

The term "$(C_3-C_6)$cycloalkyl" refers to a known ring system saturated, unsaturated or aromatic comprising one or more rings and from 3 to 6 ring members selected from C, CH, O, N, NH, and S. Non limiting examples of $(C_3-C_6)$ cycloalkyl rings include cyclopropyl, cyclobutyl, cyclopentyl, cyclopentenyl, cyclohexyl, cyclohexenyl, phenyl, aziridinyl, oxiranyl, dihydrofuryl, dihydropyranyl, dihydrothienyl, dithiazolyl, furyl, homopiperidinyl, imidazolidinyl, imidazolinyl, imidazolyl, isothiazolyl, isoxazolyl, morpholinyl, oxadiazolyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolinyl, pyrrolyl, tetrahydrofuryl, tetrazolyl, thiadiazolyl, thiazolidinyl, thiazolyl, thienyl, thiomorholinyl, triazolyl, and the like. In the case of a ring system containing a CH member and a NH member, the ring may be attached to the rest of the molecule through the C or the N atom.

The term "$(C_6-C_{12})$aryl" refers to a aromatic known ring system comprising one or more rings and from 6 to 12 ring members, wherein all the ring members comprise carbon atoms. Examples of $(C_6-C_{12})$aryl include phenyl and naphthalene.

The term "$(C_5-C_{12})$heteroaryl" refers to a known aromatic ring system comprising one or more rings and from 5 to 12 ring members, wherein one or more of the ring members, preferably 1, 2, 3, or 4 ring members, are selected from NH, N, O, and S, where chemically possible. The remaining ring members of the heteroaryl ring are independently selected from C, CH, O, N, NH, and S. Non limiting examples of $(C_5-C_{12})$heteroaryl rings include furan-2-yl, furan-3-yl, thiophen-2-yl, thiophen-2-yl, indol-2-yl, imidazolyl, isothiazolyl, isoxazolyl, oxazolyl, pyrazolyl, 2-pyridyl, 3-pyridyl, pyrrolyl, tetrazolyl, thiadiazolyl, thiazolyl, triazolyl, and the like. In the case of a ring system containing a CH member and a NH member, the ring may be attached to the rest of the molecule through the C or the N atom.

The groups $(C_p-C_n)$alkyl, unsaturated $(C_p-C_n)$hydrocarbon, $(C_3-C_6)$cycloalkyl, $(C_6-C_{12})$aryl, and $(C_5-C_{12})$heteroaryl as defined in the present invention may be unsubstituted or substituted as described herein, being the substituents placed on any available position.

The term "known ring system" as used herein refers to a ring system which is chemically feasible and is known in the art and so intends to exclude those ring systems that are not chemically possible.

In the embodiments of the invention referring to the compounds of formula (I), where the substitution or unsubstitution of a certain group is not specified, e.g. either by indicating a certain substitution for that group or by indicating that the group is unsubstituted, it has to be understood that the possible substitution of this group is the one as in the definition of the formula (I). The same applies when in specific group is said to be "optionally substituted".

The present invention also includes the tautomeric forms of the compounds of formula (I). The term "tautomeric isomers" means isomers, the structures of which differ in the position of an atom, generally a hydrogen atom, and of one or more multiple bonds, and which are capable of easily and reversibly changing from one to another. The tautomers are used indistinctly in the present application. Thus, as an example, a hydroxyphenyl group has to be considered equivalent to its tautomeric form: cyclohexa-2,4-dienone. All tautomers are to be considered equivalent for the purposes of the invention.

There is no limitation on the type of salt of the compounds of the invention that can be used, provided that these are pharmaceutically, cosmetically or veterinary acceptable when they are used for therapeutic purposes. The term "pharmaceutically, cosmetically or veterinary acceptable salts", embraces salts commonly used to form alkali metal salts and to form addition salts of free acids or free bases.

The preparation of pharmaceutically, cosmetically or veterinary acceptable salts of the compounds of formula (I) can be carried out by methods known in the art. For instance, they can be prepared from the parent compound, which contains a basic or acidic moiety, by conventional chemical methods. Generally, such salts are, for example, prepared by reacting the free acid or base forms of these compounds with a stoichiometric amount of the appropriate pharmaceutically, cosmetically or veterinary acceptable base or acid in water or in an organic solvent or in a mixture of them. The compounds of formula (I) and their salts may differ in some physical properties but they are equivalent for the purposes of the present invention.

The compounds of the invention may be in crystalline form either as free solvation compounds or as solvates (e.g. hydrates) and it is intended that both forms are within the scope of the present invention. Methods of solvation are generally known within the art. In general, the solvated forms with pharmaceutically, cosmetically or veterinary acceptable solvents such as water, ethanol and the like are equivalent to the unsolvated form for the purposes of the invention.

Some compounds of the invention can have chiral centres that can give rise to various stereoisomers. As used herein, the term "stereoisomer" refers to all isomers of individual compounds that differ only in the orientation of their atoms in space. The term stereoisomer includes mirror image isomers (enantiomers), mixtures of mirror image isomers (racemates, racemic mixtures), geometric (cis/trans or syn/anti or E/Z) isomers, and isomers of compounds with more than one chiral center that are not mirror images of one another (diastereoisomers). The present invention relates to each of these stereoisomers and also mixtures thereof.

Diastereoisomers and enantiomers can be separated by conventional techniques such as chromatography or fractional crystallization. Optical isomers can be resolved by conventional techniques of optical resolution to give optically pure isomers. This resolution can be carried out on any chiral synthetic intermediates or on compounds of the invention. Optically pure isomers can also be individually obtained using enantiospecific synthesis.

In all embodiments of the invention referring to the compounds of formula (I), the pharmaceutically, cosmetically or veterinary acceptable salts thereof and the stereoisomers or mixtures of stereoisomers, either of any of the compounds of formula (I) or of any of their pharmaceutically acceptable salts are always contemplated even if they are not specifically mentioned.

In the first aspect of the invention, the compound of the invention is other than the ones listed in Table 1:

TABLE 1

| CAS Registry Number | Compound name | Chemical formula | Bibliographic references |
|---|---|---|---|
| 1212774-95-2 | (3,4-dimethoxy-phenethylcarbamoyl)-methyl but-2-enoate | | None |
| 1211311-67-9 | (3,4-dimethoxy-phenethylcarbamoyl)-methyl 4-methyl-pentanoate | | None |
| 1211015-65-4 | (3,4-dimethoxybenzyl-carbamoyl)methyl 3,3-dimethylbutanoate | | None |

TABLE 1-continued

| CAS Registry Number | Compound name | Chemical formula | Bibliographic references |
|---|---|---|---|
| 1210984-84-1 | (3,4-dimethoxy-phenethylcarbamoyl)-methyl 3,3-dimethylbutanoate | | None |
| 1209697-03-9 | (3,4-dimethoxy-phenethylcarbamoyl)-methyl 3-methylbut-2-enoate | | None |
| 1208873-92-0 | (3,4-dimethoxy-benzylcarbamoyl)-methyl 4-methyl-pentanoate | | None |
| 1004704-89-5 | (3,4-dimethoxy-benzylcarbamoyl)-methyl 3-methylbut-2-enoate | | None |
| 1004188-90-2 | (2E,4E)-(3,4-dimethoxybenzyl-carbamoyl)methyl hexa-2,4-dienoate | | None |
| 1002977-88-9 | (3,4-dimethoxy-benzylcarbamoyl)-methyl butyrate | | None |
| 923254-60-8 | (3,4-dimethoxy-phenethylcarbamoyl)-methyl butyrate | | None |
| 878612-84-1 | (3,4-dimethoxy-phenethylcarbamoyl)-methyl hexa-2,4-dienoate | | None |

TABLE 1-continued

| CAS Registry Number | Compound name | Chemical formula | Bibliographic references |
|---|---|---|---|
| 804505-61-1 | (3,4-dimethoxy-phenethylcarbamoyl)-methyl 2-ethylbutanoate | | None |
| 750622-05-0 | (3,4-dimethoxybenzyl-carbamoyl)methyl but-2-enoate | | None |
| 480393-36-0 | (3,4-dimethoxy-benzylcarbamoyl)methyl but-3-enoate | | None |
| 479705-83-4 | (3,4-dimethoxybenzyl-carbamoyl)methyl but-3-enoate | | None |
| 474666-71-2 | (3,4-dimethoxybenzyl-carbamoyl)methyl undec-10-enoate | | None |
| 438605-31-3 | (3,4-dimethoxybenzyl-carbamoyl)methyl 2-methylpentanoate | | None |
| 182553-24-8 | 2-(3,4-dimethoxy-phenethylcarbamoyl)-propan-2-yl pentanoate | | J. Org. Chem. 1997, 62, 2080-2092. Tetrahedron Letters 1996, Vol. 37, No. 34, pp. 6193-6196. |

As can be seen in the table above, all the cited compounds except the last one are commercial products with no associated bibliographic references. Compound with CAS RN 182553-24-8 is disclosed in the references J. Org. Chem. 1997, 62, 2080-2092 and Tetrahedron Letters 1996, Vol. 37, No. 34, pp. 6193-6196. These documents only disclose the chemical synthesis of compounds and therefore, do not belong to the chemical field of the invention, i.e., none of these documents describes the ability of these compounds to modulate TRPV1, nor their use in the treatment and/or prevention of related conditions and/or diseases.

In one embodiment, optionally in combination with one or more features of the various embodiments described above or below, the invention relates to a compound of formula (I) as previously described, wherein m is an integer selected from 1 to 2. In a more particular embodiment, m is 1. In another more particular embodiment, m is 2.

In another embodiment, optionally in combination with one or more features of the various embodiments described above or below, the invention relates to a compound of formula (I) as previously described, wherein $R^1$ is selected from the group consisting of H, optionally substituted $(C_1\text{-}C_8)$alkyl, and optionally substituted unsaturated $(C_2\text{-}C_8)$ hydrocarbon. More particularly, $R^1$ is H or optionally substituted $(C_1\text{-}C_8)$alkyl. Even more particularly, optionally substituted $(C_1\text{-}C_8)$alkyl is optionally substituted $(C_1\text{-}C_6)$ alkyl. Even more particularly, optionally substituted $(C_1\text{-}C_8)$ alkyl is optionally substituted $(C_1\text{-}C_3)$alkyl. Even more particularly, $R^1$ is H or methyl.

In another embodiment, optionally in combination with one or more features of the various embodiments described above or below, the invention relates to a compound of formula (I) as previously described, wherein $R^2$ is selected from the group consisting of H, optionally substituted $(C_1\text{-}C_8)$alkyl, and optionally substituted unsaturated $(C_2\text{-}C_8)$ hydrocarbon. More particularly, $R^2$ is H or optionally substituted $(C_1\text{-}C_8)$alkyl. Even more particularly, optionally substituted $(C_1\text{-}C_8)$alkyl is optionally substituted $(C_1\text{-}C_6)$ alkyl. Even more particularly, optionally substituted $(C_1\text{-}C_8)$ alkyl is optionally substituted $(C_1\text{-}C_3)$alkyl. Even more particularly, $R^2$ is H or methyl, even more particularly $R^2$ is H.

In another embodiment, optionally in combination with one or more features of the various embodiments described above or below, the invention relates to a compound of formula (I) as previously described, wherein $R^3$ is H.

In another embodiment, optionally in combination with one or more features of the various embodiments described above or below, the invention relates to a compound of formula (I) as previously described, wherein $R^3$ is halogen, more particularly iodine.

In another embodiment, optionally in combination with one or more features of the various embodiments described above or below, the invention relates to a compound of formula (I) as previously described, wherein $R^4$ is selected from the group consisting of H, optionally substituted $(C_1\text{-}C_8)$alkyl, and optionally substituted unsaturated $(C_2\text{-}C_8)$ hydro-carbon. More particularly, $R^4$ is H or optionally substituted $(C_1\text{-}C_8)$alkyl. Even more particularly, optionally substituted $(C_1\text{-}C_8)$alkyl is optionally substituted $(C_1\text{-}C_6)$ alkyl. Even more particularly, optionally substituted $(C_1\text{-}C_8)$ alkyl is optionally substituted $(C_1\text{-}C_3)$alkyl. Even more particularly, $R^4$ is H.

In another embodiment, optionally in combination with one or more features of the various embodiments described above or below, the invention relates to a compound of formula (I) as previously described, wherein $R^6$ and $R^{6'}$ are independently selected from the group consisting of H, optionally substituted $(C_1\text{-}C_8)$alkyl, and optionally substituted unsaturated $(C_2\text{-}C_8)$hydrocarbon. More particularly, $R^6$ and $R^{6'}$ are independently H or optionally substituted $(C_1\text{-}C_8)$alkyl. Even more particularly, optionally substituted $(C_1\text{-}C_8)$alkyl is optionally substituted $(C_1\text{-}C_6)$alkyl. Even more particularly, optionally substituted $(C_1\text{-}C_8)$alkyl is optionally substituted $(C_1\text{-}C_3)$alkyl. Even more particularly, $R^6$ and $R^{6'}$ are H.

In another embodiment, optionally in combination with one or more features of the various embodiments described above or below, the invention relates to a compound of formula (I) as previously described, wherein $R^5$ is selected from the group consisting of optionally substituted $(C_3\text{-}C_{28})$ alkyl, and optionally substituted unsaturated $(C_3\text{-}C_{28})$hydro-carbon. More particularly, $R^5$ is optionally substituted $(C_6\text{-}C_{28})$alkyl or optionally substituted unsaturated $(C_6\text{-}C_{28})$ hydrocarbon. Even more particularly $R^5$ is optionally substituted $(C_9\text{-}C_{26})$alkyl or optionally substituted unsaturated $(C_9\text{-}C_{26})$hydrocarbon.

In another embodiment, optionally in combination with one or more features of the various embodiments described above or below, the invention relates to a compound of formula (I) as previously described, wherein $R^5$ is selected from the group consisting of: propyl, butyl, 2-methylpropyl, pentyl, penta-1,3-dienyl, hexyl, heptyl, octyl, 2,6-dimethylhepta-1,5-dienyl, nonyl, undecyl, tetradecyl, heptadecyl, heptadec-8-enyl, 11-hydroxyheptadec-8-enyl, henicos-12-enyl, nonadeca-4,7,10,13-tetraenyl, 3,7,12,16,20-pentamethylhenicosa-3,7,11,15,19-pentaenyl, icosa-5,8,11,14-tetraen-2-yl, and heptadec-8-enyl. More particularly, $R^5$ is 2,6-dimethylhepta-1,5-dienyl, undecyl, and 3,7,12,16,20-pentamethylhenicosa-3,7,11,15,19-pentaenyl.

In another embodiment, optionally in combination with one or more features of the various embodiments described above or below, the invention relates to a compound of formula (I) as previously described, wherein $R^5$ is selected from the group consisting of:

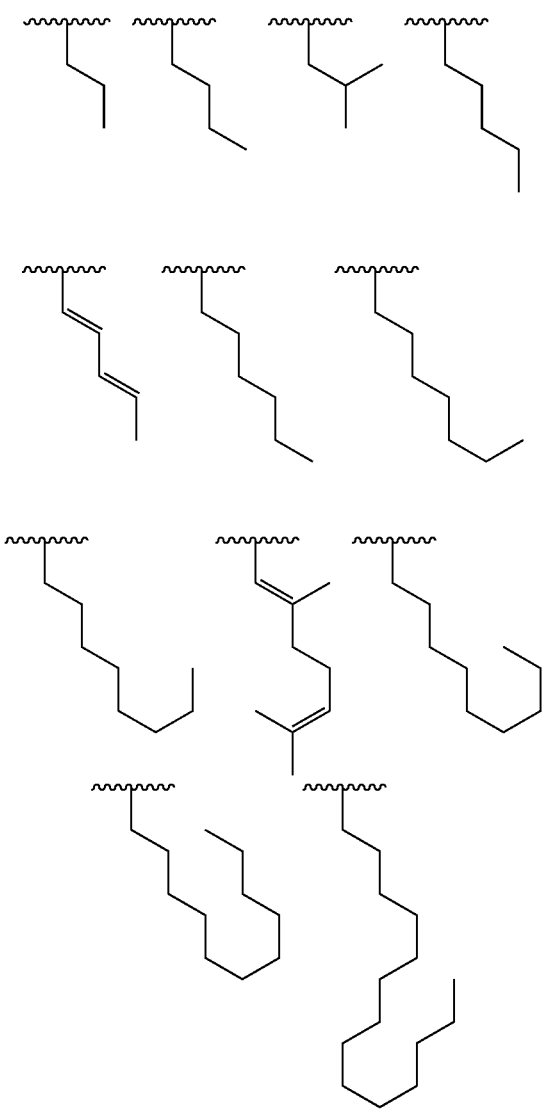

-continued

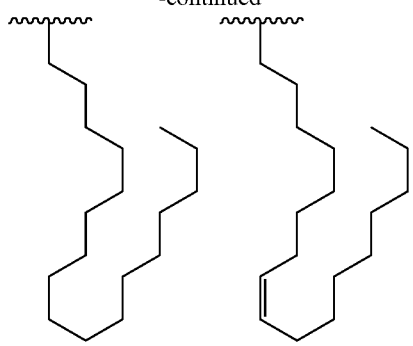

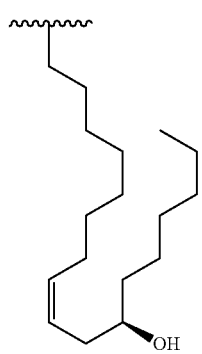
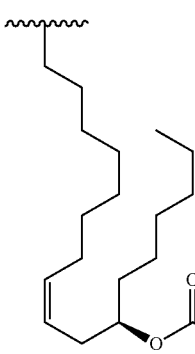

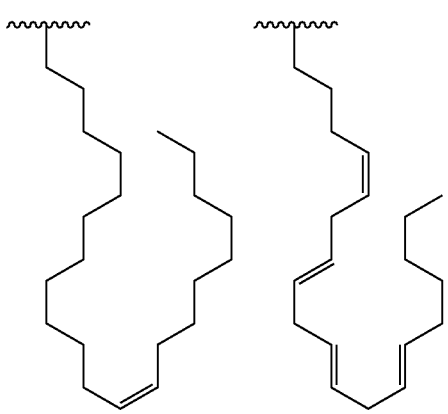

-continued

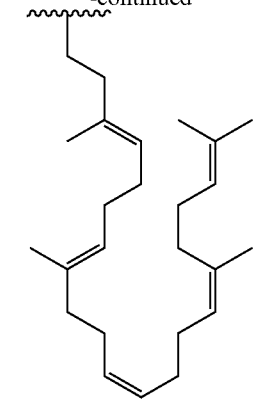

In another embodiment, optionally in combination with one or more features of the various embodiments described above or below, the invention relates to a compound of formula (I) as previously described, wherein $R^5$ is selected from the group consisting of:

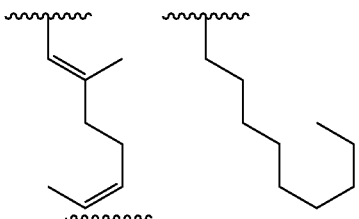

In another embodiment of the invention, the compound of formula (I) is selected from the group consisting of:

| Comp. | Name | Structure |
|---|---|---|
| 16 | 2-((4-hydroxy-3-methoxy-benzyl)amino)-2-oxoethyl butyrate | 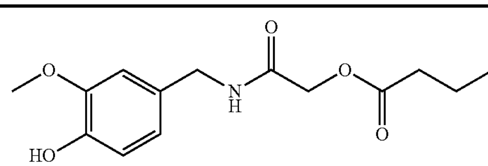 |
| 17 | 2-((4-hydroxy-2-iodo-5-methoxybenzyl)amino)-2-oxoethyl butyrate | 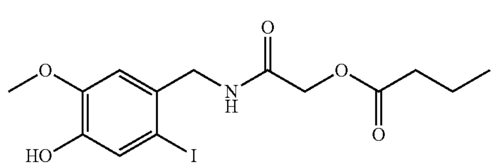 [SMILES: CCCC(=O)OCC(=O)NCc1cc(OC)c(O)cc1I] |

-continued

| Comp. | Name | Structure |
|---|---|---|
| 18 | 2-((4-hydroxy-3-methoxy-benzyl)amino)-2-oxoethyl pentanoate | 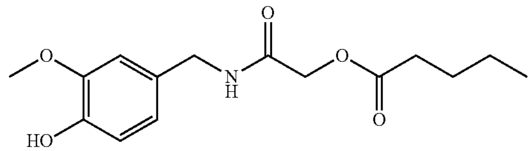 [SMILES: CCCCC(=O)OCC(=O)NCc1ccc(O)c(OC)c1] |
| 19 | 2-((4-hydroxy-2-iodo-5-methoxybenzyl)amino)-2-oxoethyl pentanoate | 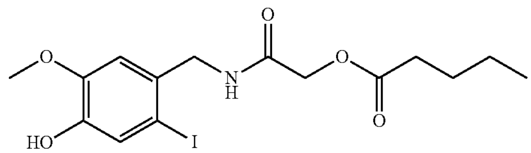 [SMILES: CCCCC(=O)OCC(=O)NCc1cc(OC)c(O)cc1I] |
| 20 | 2-((4-hydroxy-3-methoxy-benzyl)amino)-2-oxoethyl 3-methylbutanoate | 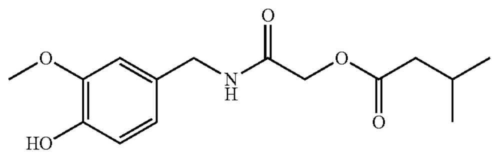 [SMILES: COc1cc(CNC(=O)COC(=O)CC(C)C)ccc1O] |
| 21 | 2-((4-hydroxy-2-iodo-5-methoxybenzyl)amino)-2-oxoethyl 3-methyl-butanoate | 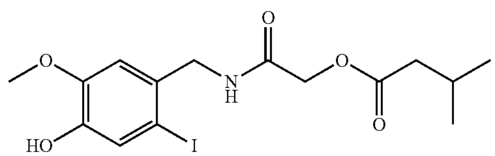 [SMILES: COc1cc(CNC(=O)COC(=O)CC(C)C)c(I)cc1O] |
| 22 | 2-((4-hydroxy-3-methoxy-benzyl)amino)-2-oxoethyl hexanoate | 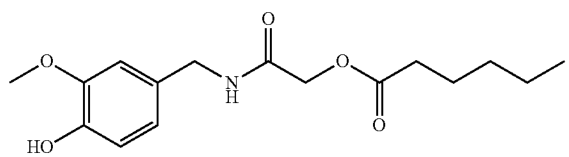 [SMILES: CCCCCC(=O)OCC(=O)NCc1ccc(O)c(OC)c1] |
| 23 | 2-((4-hydroxy-2-iodo-5-methoxybenzyl)amino)-2-oxoethyl hexanoate | 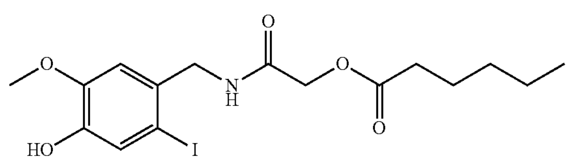 [SMILES: CCCCCC(=O)OCC(=O)NCc1cc(OC)c(O)cc1I] |
| 24 | (2E,4E)-2-((4-hydroxy-3-methoxybenzyl)amino)-2-oxoethyl hexa-2,4-dienoate | 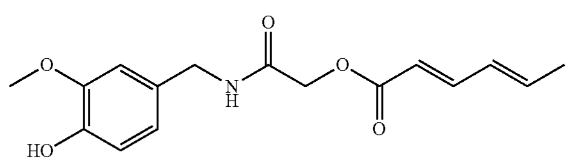 [SMILES: C/C=C/C=C/C(=O)OCC(=O)NCc1ccc(O)c(OC)c1] |
| 25 | (2E,4E)-2-((4-hydroxy-2-iodo-5-methoxybenzyl)amino)-2-oxoethyl hexa-2,4-dienoate | 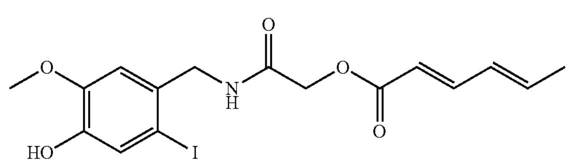 [SMILES: C/C=C/C=C/C(=O)OCC(=O)NCc1cc(OC)c(O)cc1I] |
| 26 | 2-((4-hydroxy-3-methoxy-benzyl)amino)-2-oxoethyl heptanoate | 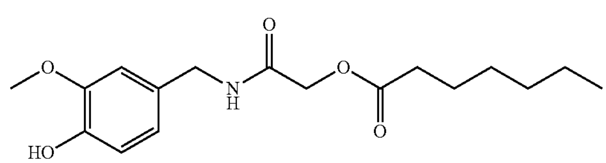 [SMILES: CCCCCCC(=O)OCC(=O)NCc1ccc(O)c(OC)c1] |

-continued

| Comp. | Name | Structure |
|---|---|---|
| 27 | 2-((4-hydroxy-2-iodo-5-methoxybenzyl)amino)-2-oxoethyl heptanoate | 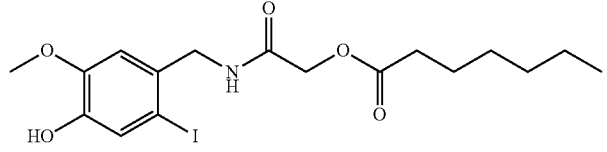 [SMILES: CCCCCCC(=O)OCC(=O)NCc1cc(OC)c(O)cc1I] |
| 28 | 2-((4-hydroxy-3-methoxy-benzyl)amino)-2-oxoethyl octanoate | 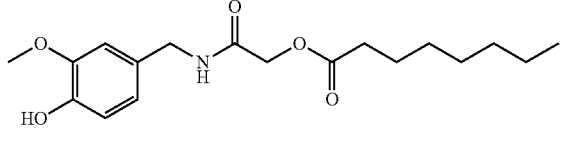 [SMILES: CCCCCCCC(=O)OCC(=O)NCc1ccc(O)c(OC)c1] |
| 29 | 2-((4-hydroxy-2-iodo-5-methoxybenzyl)amino)-2-oxoethyl octanoate | 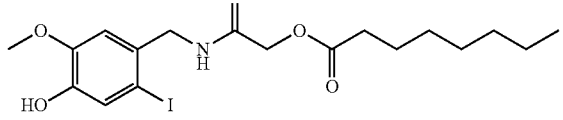 |
| 30 | 2-((4-hydroxy-3-methoxybenzyl)amino)-2-oxoethyl nonanoate | 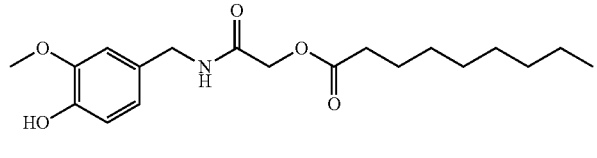 [SMILES: CCCCCCCCC(=O)OCC(=O)NCc1ccc(O)c(OC)c1] |
| 31 | 2-((4-hydroxy-2-iodo-5-methoxybenzyl)amino)-2-oxoethyl nonanoate | 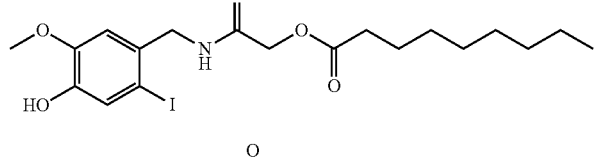 |
| 32 | (E)-2-((4-hydroxy-3-methoxy-benzyl)amino)-2-oxoethyl 3,7-dimethylocta-2,6-dienoate | 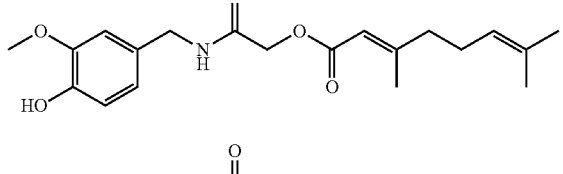 |
| 33 | (E)-2-((4-hydroxy-2-iodo-5-methoxybenzyl)amino)-2-oxoethyl 3,7-dimethylocta-2,6-dienoate | 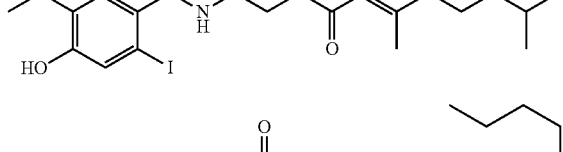 |
| 34 | 2-((4-hydroxy-3-methoxy-benzyl)amino)-2-oxoethyl decanoate | 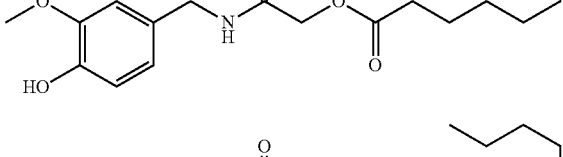 |
| 35 | 2-((4-hydroxy-2-iodo-5-methoxybenzyl)amino)-2-oxoethyl decanoate | 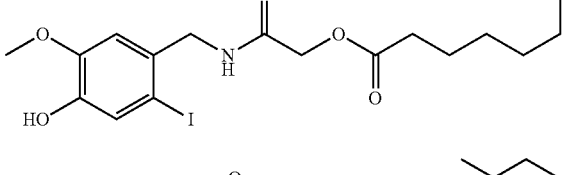 |
| 36 | 2-((4-hydroxy-3-methoxy-benzyl)amino)-2-oxoethyl dodecanoate | 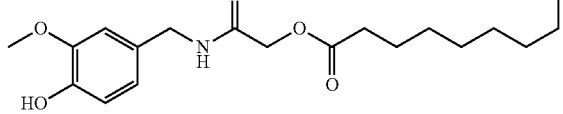 |

-continued

| Comp. | Name | Structure |
|---|---|---|
| 37 | 2-((4-hydroxy-2-iodo-5-methoxybenzyl)amino)-2-oxoethyl dodecanoate | 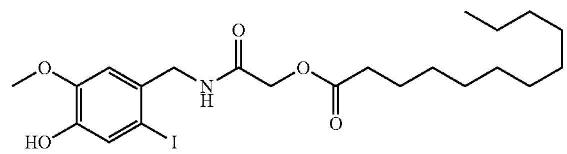 [SMILES: CCCCCCCCCCCC(=O)OCC(=O)NCc1cc(OC)c(O)cc1I] |
| 38 | 2-((4-hydroxy-3-methoxybenzyl)amino)-2-oxoethyl pentadecanoate | 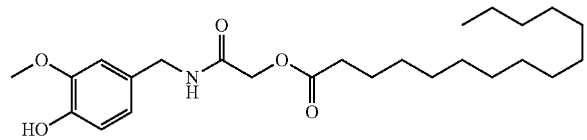 [SMILES: CCCCCCCCCCCCCCC(=O)OCC(=O)NCc1ccc(O)c(OC)c1] |
| 39 | 2-((4-hydroxy-2-iodo-5-methoxybenzyl)amino)-2-oxoethyl pentadecanoate | 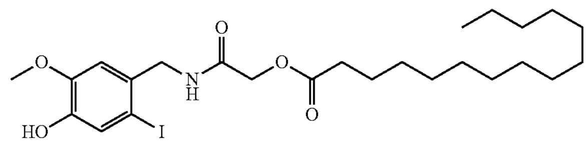 [SMILES: CCCCCCCCCCCCCCC(=O)OCC(=O)NCc1cc(OC)c(O)cc1I] |
| 40 | 2-((4-hydroxy-3-methoxybenzyl)amino)-2-oxoethyl stearate | 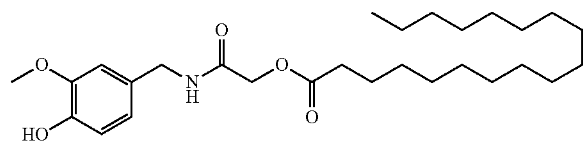 |
| 41 | 2-((4-hydroxy-2-iodo-5-methoxybenzyl)amino)-2-oxoethyl stearate | 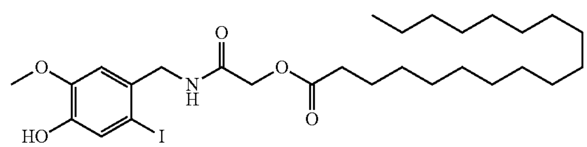 [SMILES: CCCCCCCCCCCCCCCCCC(=O)OCC(=O)NCc1cc(OC)c(O)cc1I] |
| 42 | 2-((4-hydroxy-3-methoxybenzyl)amino)-2-oxoethyl oleate | 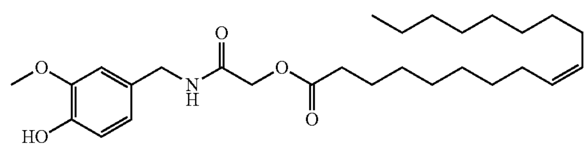 [SMILES: CCCCCCCC/C=C\CCCCCCCC(=O)OCC(=O)NCc1ccc(O)c(OC)c1] |
| 43 | 2-((4-hydroxy-2-iodo-5-methoxybenzyl)amino)-2-oxoethyl oleate | 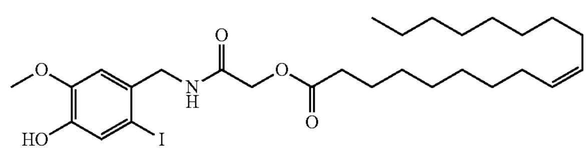 [SMILES: CCCCCCCC/C=C\CCCCCCCC(=O)OCC(=O)NCc1cc(OC)c(O)cc1I] |
| 44 | (R,Z)-2-((4-hydroxy-3-methoxybenzyl)amino)-2-oxoethyl 12-hydroxyoctadec-9-enoate | 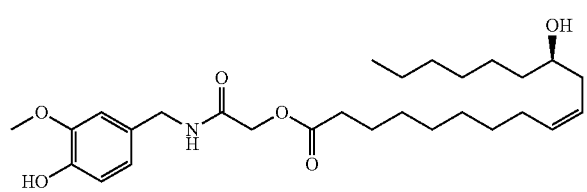 [SMILES: CCCCCC[C@@H](O)C/C=C\CCCCCCCC(=O)OCC(=O)NCc1ccc(O)c(OC)c1] |
| 45 | (R,Z)-2-((4-hydroxy-2-iodo-5-methoxybenzyl)amino)-2-oxoethyl 12-hydroxyoctadec-9-enoate | 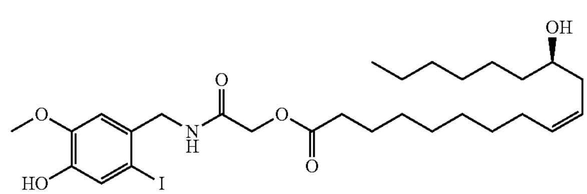 [SMILES: CCCCCC[C@@H](O)C/C=C\CCCCCCCC(=O)OCC(=O)NCc1cc(OC)c(O)cc1I] |

-continued

| Comp. | Name | Structure |
|---|---|---|
| 46 | (Z)-2-((4-hydroxy-3-methoxybenzyl)amino)-2-oxoethyl 12-(2-phenylacetoxy)octadec-9-enoate | 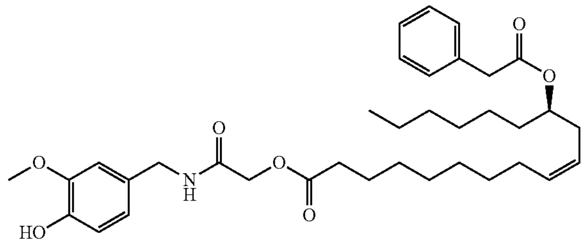 [SMILES: CCCCCC[C@H](C/C=C\CCCCCCCC(=O)OCC(=O)NCc1ccc(O)c(OC)c1)OC(=O)Cc1ccccc1] |
| 47 | (Z)-2-((4-hydroxy-2-iodo-5-methoxybenzyl)amino)-2-oxoethyl 12-(2-phenylacetoxy)octadec-9-enoate | 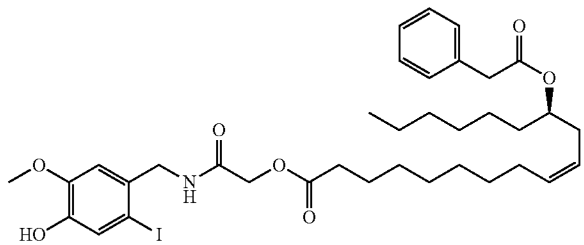 [SMILES: CCCCCC[C@H](C/C=C\CCCCCCCC(=O)OCC(=O)NCc1cc(OC)c(O)cc1I)OC(=O)Cc1ccccc1] |
| 48 | (Z)-2-((4-hydroxy-3-methoxybenzyl)amino)-2-oxoethyl docos-13-enoate | 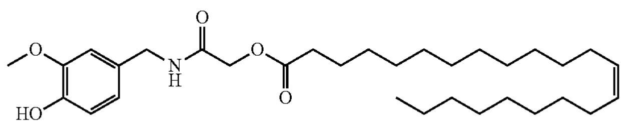 [SMILES: CCCCCCCC/C=C\CCCCCCCCCCCC(=O)OCC(=O)NCc1ccc(O)c(OC)c1] |
| 49 | (Z)-2-((4-hydroxy-2-iodo-5-methoxybenzyl)amino)-2-oxoethyl docos-13-enoate | 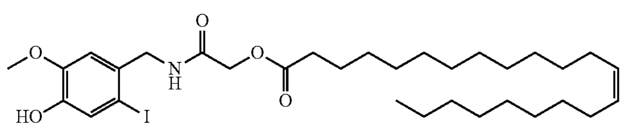 [SMILES: CCCCCCCC/C=C\CCCCCCCCCCCC(=O)OCC(=O)NCc1cc(OC)c(O)cc1I] |
| 50 | (5Z,8Z,11Z,14Z)-2-((4-hydroxy-3-methoxybenzyl)amino)-2-oxoethyl icosa-5,8,11,14-tetraenoate | 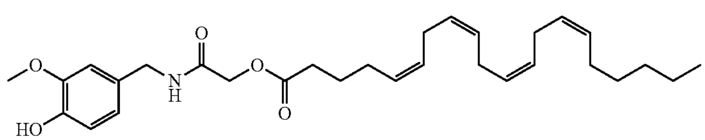 [SMILES: CCCCC/C=C\C/C=C\C/C=C\C/C=C\CCCC(=O)OCC(=O)NCc1ccc(O)c(OC)c1] |
| 51 | (5Z,8Z,11Z,14Z)-2-((4-hydroxy-2-iodo-5-methoxybenzyl)amino)-2-oxoethyl icosa-5,8,11,14-tetraenoate | 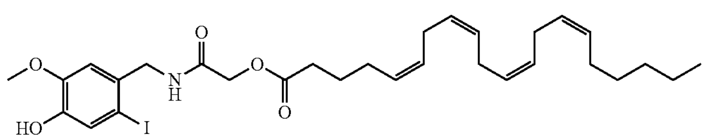 [SMILES: CCCCC/C=C\C/C=C\C/C=C\C/C=C\CCCC(=O)OCC(=O)NCc1cc(OC)c(O)cc1I] |
| 52 | (4E,8E,12E,16E)-2-((4-hydroxy-3-methoxybenzyl)amino)-2-oxoethyl 4,8,13,17,21-pentamethyldocosa-4,8,12,16,20-pentaenoate | 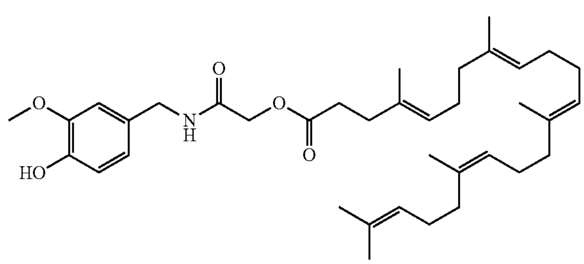 [SMILES: COc1cc(CNC(=O)COC(=O)CC/C(C)=C/CC/C(C)=C/CC/C=C(\C)CC/C=C(/C)CCC=C(C)C)ccc1O] |
| 53 | (4E,8E,12E,16E)-2-((4-hydroxy-2-iodo-5-methoxybenzyl)amino)-2-oxoethyl 4,8,13,17,21-pentamethyldocosa-4,8,12,16,20-pentaenoate | 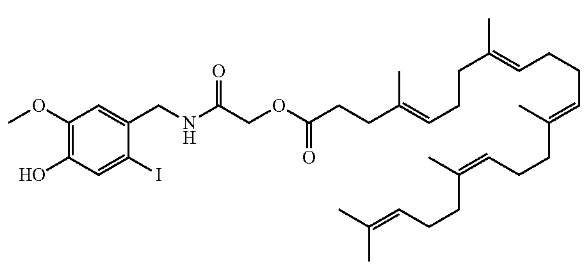 [SMILES: COc1cc(CNC(=O)COC(=O)CC/C(C)=C/CC/C(C)=C/CC/C=C(\C)CC/C=C(/C)CCC=C(C)C)c(I)cc1O] |

-continued

| Comp. | Name | Structure |
|---|---|---|
| 54 | (E)-2-((3,4-dihydroxybenzyl)-amino)-2-oxoethyl 3,7-dimethylocta-2,6-dienoate | 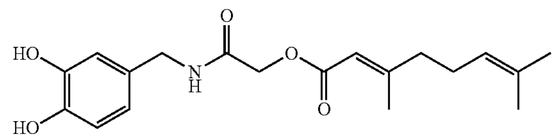 [SMILES: CC(C)=CCC/C(C)=C/C(=O)OCC(=O)NCc1ccc(O)c(O)c1] |
| 55 | (E)-2-((4,5-dihydroxy-2-iodo-benzyl)amino)-2-oxoethyl 3,7-dimethylocta-2,6-dienoate | 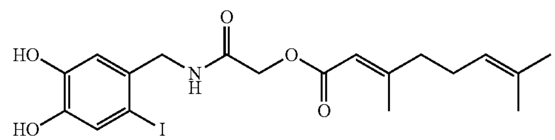 [SMILES: CC(C)=CCC/C(C)=C/C(=O)OCC(=O)NCc1cc(O)c(O)cc1I] |
| 56 | (4E,8E,12E,16E)-2-((3,4-dihydroxybenzyl)amino)-2-oxoethyl 4,8,13,17,21-pentamethyldocosa-4,8,12,16,20-pentaenoate | 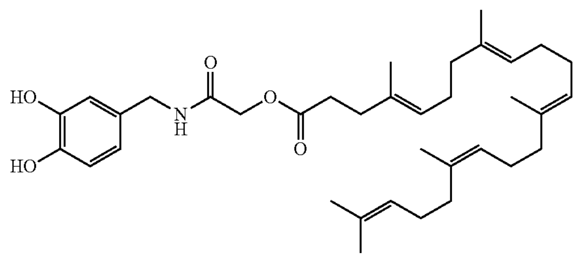 [SMILES: CC(C)=CCC/C(C)=C\CC/C(C)=C/CC/C=C(\C)CC/C=C(\C)CCC(=O)OCC(=O)NCc1ccc(O)c(O)c1] |
| 57 | (4E,8E,12E,16E)-2-((4,5-dihydroxy-2-iodobenzyl)-amino)-2-oxoethyl 4,8,13,17,21-pentamethyl-docosa-4,8,12,16,20-pentaenoate | 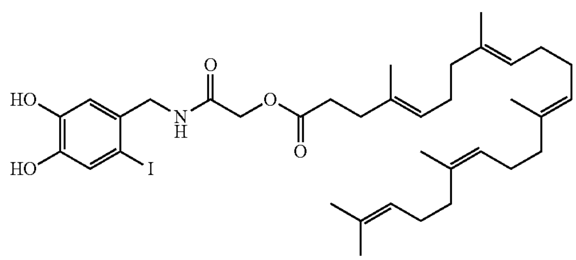 [SMILES: CC(C)=CCC/C(C)=C\CC/C(C)=C/CC/C=C(\C)CC/C=C(\C)CCC(=O)OCC(=O)NCc1cc(O)c(O)cc1I] |
| 58 | (E)-2-((3,4-dihydroxy-phenethyl)amino)-2-oxoethyl 3,7-dimethylocta-2,6-dienoate | 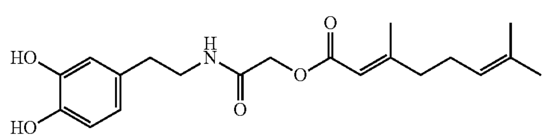 [SMILES: CC(C)=CCC/C(C)=C/C(=O)OCC(=O)NCCc1ccc(O)c(O)c1] |
| 59 | (E)-2-((4,5-dihydroxy-2-iodophenethyl)amino)-2-oxoethyl 3,7-dimethylocta-2,6-dienoate | 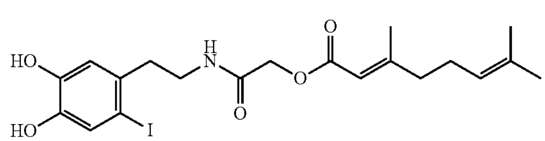 [SMILES: CC(C)=CCC/C(C)=C/C(=O)OCC(=O)NCCc1cc(O)c(O)cc1I] |
| 60 | (4E,8E,12E,16E)-2-((3,4-dihydroxyphenethyl)amino)-2-oxoethyl 4,8,13,17,21-pentamethyldocosa-4,8,12,16,20-pentaenoate | 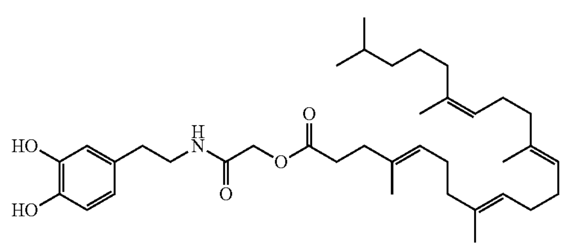 [SMILES: C/C(=C/CC/C(C)=C/CC/C=C(\C)CC/C=C(\C)CCC(=O)OCC(=O)NCCc1ccc(O)c(O)c1)CCCC(C)C] |
| 61 | (4E,8E,12E,16E)-2-((4,5-dihydroxy-2-iodophenethyl)-amino)-2-oxoethyl 4,8,13,17,21-pentamethyl-docosa-4,8,12,16,20-pentaenoate | 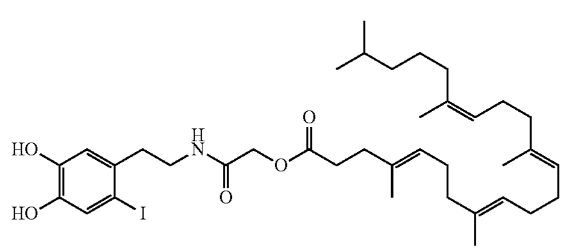 [SMILES: C/C(=C/CC/C(C)=C/CC/C=C(\C)CC/C=C(\C)CCC(=O)OCC(=O)NCCc1cc(O)c(O)cc1I)CCCC(C)C] |

| Comp. | Name | Structure |
|---|---|---|
| 62 | 2-((3,4-dihydroxyphenethyl)-amino)-2-oxoethyl oleate | 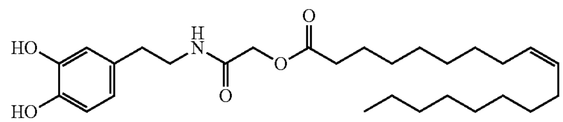 [SMILES: CCCCCCCC/C=C\CCCCCCCC(=O)OCC(=O)NCCc1ccc(O)c(O)c1] |
| 63 | 2-((4,5-dihydroxy-2-iodophenethyl)amino)-2-oxoethyl oleate | 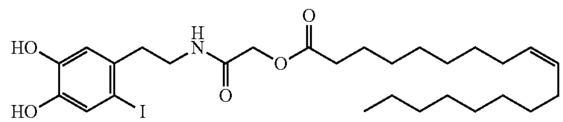 [SMILES: CCCCCCCC/C=C\CCCCCCCC(=O)OCC(=O)NCCc1cc(O)c(O)cc1I] |
| 64 | (5Z,8Z,11Z,14Z)-2-((3,4-dihydroxyphenethyl)amino)-2-oxoethyl icosa-5,8,11,14-tetraenoate | 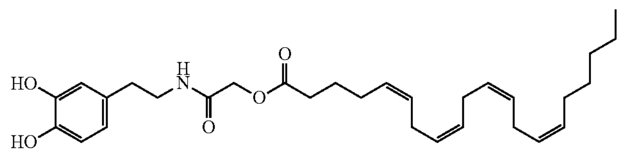 [SMILES: CCCCC/C=C\C/C=C\C/C=C\C/C=C\CCCC(=O)OCC(=O)NCCc1ccc(O)c(O)c1] |
| 65 | (5Z,8Z,11Z,14Z)-2-((4,5-dihydroxy-2-iodophenethyl)-amino)-2-oxoethyl icosa-5,8,11,14-tetraenoate | 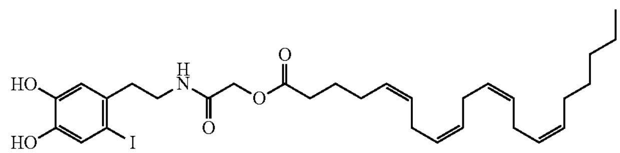 [SMILES: CCCCC/C=C\C/C=C\C/C=C\C/C=C\CCCC(=O)OCC(=O)NCCc1cc(O)c(O)cc1I] |

It also forms part of the invention a process for the preparation of a compound of formula (I) as defined above by coupling of a compound of formula (II) with a compound of formula (III) in the presence of formaldehyde as shown in the following scheme:

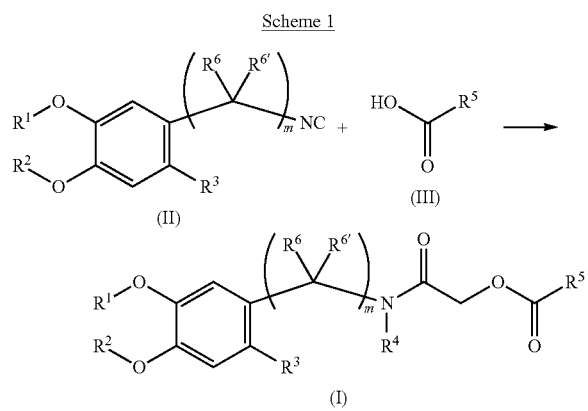

Scheme 1 to give rise to a compound of formula (I) wherein $R^4$ is H and $R^1$, $R^2$, $R^3$, $R^5$, $R^6$, $R^{6'}$ and m are as defined above. This conversion (Passerini multicomponent reaction) is carried out in the presence of a suitable solvent, such as e.g. dichloromethane, at a suitable temperature, preferably under reflux.

In the case of $R^1$ and/or $R^2$ being hydrogen, the above conversion can also be carried out using a precursor of a compound of formula (II), wherein the hydroxy group or groups are conveniently protected with a protective group. After the reaction with the compound of formula (III) in the presence of formaldehyde, the protective groups are removed and, if desired, the compound of formula (I) can be converted into another compound of formula (I). The introduction and/or removal of the protective groups is carried out by standard methods well-known in the art as described for example in T. W. Green and P. G. M. Wuts, Protective Groups in Organic Chemistry (Wiley, 3rd ed. 1999, Chapter 2, pp. 17-200). Representative hydroxy protective groups include those where the hydroxy group is either acylated or alkylated such as benzyl, and trityl ethers as well as alkyl ethers, tetrahydropyranyl ethers, trialkylsilyl ethers and allyl ethers. For example, the hydroxamic acid protective group is tertbutyldimetylsilyl and the deprotection is carried out in acidic medium, for example with acetic acid in the presence of tetra-n-butylammonium fluoride (TBAF), in a suitable solvent such as tetrahydrofuran.

The compound of formula (I) wherein $R^4$ is H can be converted into a compound of formula (I) wherein $R^4$ is selected from the group consisting of $(C_1-C_8)$alkyl, unsaturated $(C_2-C_8)$hydrocarbon, $(C_3-C_6)$cycloalkyl, $(C_6-C_{12})$aryl and $(C_5-C_{12})$heteroaryl. This can be done by alkylating the compound (I) with an alkylating agent of formula $R^4X$ wherein X is a leaving group such e.g. as a halogen atom, in the presence of a base such as potassium carbonate, sodium hydride, butyl lithium or lithium diisopropylamide and a suitable solvent such as acetonitrile, tetrhydrofuran, or dimethylformamide. Conditions like solvent and temperature will depend on the base used.

Alternatively, compounds of formula (I) can be prepared by coupling an amine of formula (VI) and a compound of formula (VII) as shown in the following scheme:

Scheme 2

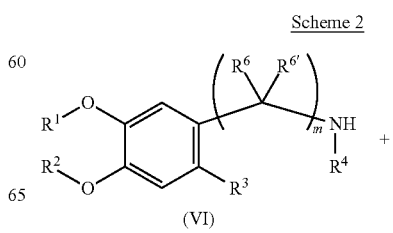

-continued

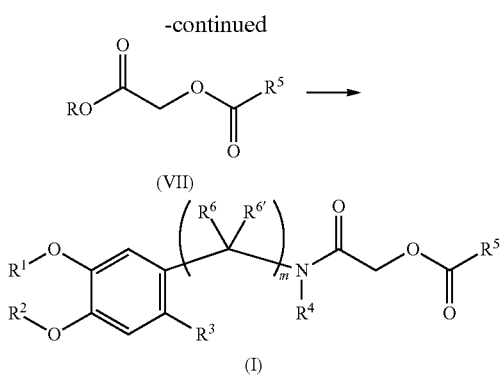

wherein $R^1$, $R^2$, $R^3$, $R^4$, $R^5$, $R^6$, $R^{6'}$ and m are as defined above, and R is H. This conversion can be carried out optionally in the presence of an activating agent such as 1-ethyl-3-(3-dimethylaminopropyl)carbodiimide hydrochloride 20 (EDC.HCl) and hydroxybenzotriazole (HOBt), preferably in the presence of a base, such as N-methylmorpholine (NMM), in a suitable solvent, such as dichloromethane, chloroform or imethylformamide, at a temperature comprised from room temperature to the temperature of the boiling point of the solvent, preferably at room temperature.

The compounds of formula (II) may be prepared from compounds of formula (IV) which can be prepared form compounds of formula (V) as shown in the scheme below:

Scheme 3

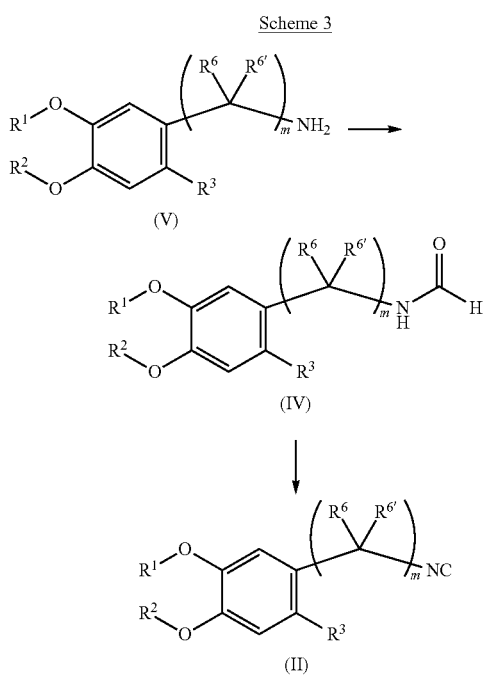

In the scheme above, $R^1$, $R^2$, $R^3$, $R^6$, $R^{6'}$ and m are as defined above. Alternatively, in the above conversions $R^1$ and/or $R^2$ can be protective groups to be converted later on into groups $R^1$ and/or $R^2$. These groups can be introduced and removed under conditions well known in the art as the ones indicated above.

The conversion of a compound of formula (V) into a compound of formula (IV) can be carried out in the presence of an ester of formic acid such as e.g. methyl formate or ethyl formate optionally in a suitable solvent, such as methanol, and optionally in the presence of a base, such as $K_2CO_3$, at a suitable temperature, preferably, at 35° C. Alternatively, a compound of formula (V) can be converted into a compound of formula (IV) by using a large excess of acetic anhydride and formic acid at 0° C. This reaction can be performed with or without solvent. If a solvent is used THF can be a good choice.

The compound of formula (IV) can be converted into a compound of formula (II) in the presence of a $POCl_3$ and a base such as triethylamine, in a suitable solvent such as dichloromethane, and a suitable temperature, preferably at 0° C.

A compound of formula (I) wherein $R^3$ is iodine can be prepared from a compound of formula (IV) wherein $R^3$ is H in the presence of iodine and silver trifluoroacetate in a suitable solvent such as chloroform. The resulting compound can be converted into a compound of formula (I) as previously defined.

The compounds of formulas (III), (V), (VI), and (VII) are commercially available or can be obtained by conventional synthetic processes. For example, compounds of formula (VI) where $R^4$ is different from H can be prepared from compounds of formula (V) by alkylation.

A compound of formula (I) may also be converted into another compound of formula (I), in one or a plurality of steps. Those skilled in the art will appreciate that other synthetic routes may be used to synthesize the compounds of the invention. Although specific starting materials and reagents are disclosed in the examples, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

The present invention also relates to a pharmaceutical, veterinary or cosmetic compositions comprising an effective amount of a compound of the invention, together with pharmaceutically, veterinary or cosmetically acceptable excipients or carriers.

The compositions of the invention may be immediate or sustained release systems.

The term "sustained release" is used herein to refer to a system for the delivery of a compound which provides for the gradual release of said compound over a period of time and preferably, but not necessarily, with relatively constant release levels of the compound at over a period of time.

Examples of sustained release or carrier systems include, without limitation, liposomes, mixed liposomes, oleosomes, niosomes, etosomes, milliparticles, microparticles, nanoparticles and solid lipid nanoparticles, nanostructured lipid carriers, sponges, cyclodextrins, vesicles, micelles, mixed micelles of surfactants, Phospholipid-surfactant mixed micelles, millispheres, microspheres and nanospheres, lipospheres, milicapsules, microcapsules and nanocapsules, as well as in microemulsions and nanoemulsions, which may be added to achieve greater penetration of the active ingredient and/or improve the pharmacokinetic and pharmacodynamic properties thereof. Preferred sustained release or carrier systems are liposomes, mixed micellar phospholipid and microemulsions, most preferably water-in-oil microemulsions with internal reverse micelle structure.

The expression "effective amount" as used herein, relates to the amount of product that provides the cosmetic or therapeutic desired effect after its application. The effective amount that provides a therapeutic effect (also cited here as therapeutically effective amount) is the amount of a compound that, when administered, is sufficient to prevent the development of, or to relieve to some degree one or more of the symptoms of the disease to which it is directed. The particular dose of compound administered according to this invention may vary according to the particular conditions surrounding the case, including the administered compound, the route and frequency of administration, age, condition of the patient, nature or severity of the condition, disorder or condition to be treated or prevented and similar considerations.

Typically, the amount of the compounds of the invention in the compositions is preferably from preferably 0.00000001% to 20% by weight with respect to the total weight of the composition; more preferably from 0.000001% to 20%, even more preferably from 0.0001 to 10%, and still more preferably from 0.0001% to 5%.

The expression "pharmaceutically or veterinary acceptable excipients or carriers" means that the excipients or carriers are suitable for the preparation of compositions for pharmaceutical or medical uses in humans and animals. Each component must be pharmaceutically acceptable in the sense of being compatible with the other ingredients of the pharmaceutical or veterinary composition. It must also be suitable for use in contact with tissues or organs of humans and animals without excessive toxicity, irritation, allergic response, immunogenicity or other problems or complications consistent with a reasonable risk/benefit relationship.

The expression "cosmetically acceptable excipients or carriers" means that the excipients or carriers are suitable for the preparation of compositions for cosmetic use. Each component must be cosmetically acceptable in the sense of being compatible with the other ingredients of the cosmetic composition. It must also be suitable for use in contact with tissues or organs of humans and animals without excessive toxicity, irritation, allergic response, immunogenicity or other problems or complications consistent with a reasonable risk/benefit relationship.

In a particular embodiment, optionally in combination with one or more features of the various embodiments described above or below, the composition is a pharmaceutical or veterinary composition which comprises a therapeutically effective amount of a compound of formula (I) as previously defined, together with one or more pharmaceutically or veterinary acceptable excipients or carriers.

In another particular embodiment, optionally in combination with one or more features of the various embodiments described above or below, the composition is a cosmetic composition which comprises an effective amount of a compound of formula (I) as previously defined, together with one or more pharmaceutically acceptable excipients or carriers.

The pharmaceutical composition may be formulated for buccal, oral, topical, or transdermal administration, including adhesive patches, non-adhesive patches, occlusive patches and the like, micro-patches. Systemic administration such as oral or parenteral administration. For the purposes of the invention, the term "parenteral" includes nasal, atrial, ophthalmic, rectal, urethral, vaginal, subcutaneous, intradermal, intravascular, intravenous, intramuscular, intraocular, intravitreal, intracorneal, intraspinal, intramedullary, Intracranial, intracervical, intracerebral, intrameningeal, intraarticular, intrahepatic, intrathoracic, intratracheal, intrathecal and intraperitoneal, as well as any other similar injection or infusion technique.

The election of the type of formulation will depend upon the nature of the active compound, the site of administration, the kinetics and duration of release of the compound of the invention, and the condition to be treated.

In a particular embodiment, optionally in combination with one or more features of the various embodiments described above or below, the composition of the invention is a topical composition.

In another particular embodiment, optionally in combination with one or more features of the various embodiments described above or below, the composition of the invention is a transdermal composition.

In another particular embodiment, optionally in combination with one or more features of the various embodiments described above or below, the composition of the invention is a buccal or oral composition.

Bucal and oral formulations include solid and liquid formulations such as tablets, capsules, pills, solutions, emulsions, syrups, elixirs and the like. The skilled in the art will know the appropriate excipients to be used in these formulations. Non-limiting examples of excipients include disintegrants such as microcrystalline cellulose, corn starch, sodium starch, glycolate, and alginic acid; binders such as starch, pregelatinized starch, polyvinyl pyrrolidone (PVP), copovidone, gum acacia, xanthan gum, gum tragacanth, cellulose derivatives, such as hydroxypropylmethyl cellulose (HPMC), hydroxypropyl cellulose (HPC), ethylcellulose (EC) and carboxymethyl cellulose (CMC); lubricants such as magnesium stearate or sodium laurilsulfate; glidants such as colloidal silicon dioxide, starch and talc, sweeteners such as sucrose, glucose, fructose, maltose, lactose, sorbitol, xylitol, mannitol, maltulose, isomaltulose, maltitol, isomaltitol, lactulose, and lactitol; coloring and flavoring agents, and the like.

Generally, topical or transdermal formulations include creams, multiple emulsions such as, for example, non-limiting emulsions of oil and/or silicone in water, emulsions of water/oil/water or water/silicone/water and emulsions and oil/water/oil or silicone/water/silicone, anhydrous compositions, aqueous dispersions, oils, milks, balms, foams, gels, pomades, powders, lotions, cream gels, hydroalcoholic solutions, hydro glycol solutions, hydrogels, liniments. soaps, shampoos, conditioners, serums, polysaccharide films, ointments, mousses, ointments powders, bars, dry, pastes, pencils and vaporizers, sprays, including "leave on" formulations and "rinse-off" formulations, wherein the compound is dispersed or dissolved in suitable excipients.

Topical or transdermal application can be incorporated by techniques known to those skilled in the art to various types of solid accessories such as, for example, and without limiting sense bandages, gauzes, t-shirts, socks, stockings, underwear, girdles, gloves, diapers, napkins, dressings, bedspreads, wipes, adhesive patches, non-adhesive patches, occlusive patches, microelectronic patches or face masks, or may be incorporated into various make-up line products such as makeup bottoms, such as fluid makeup bottoms and make-up lotions, cleansing lotions, make-up removers, concealers, eye shadows, lipsticks, lip protectors, lip gloss and powders, among others.

The topical compositions defined above comprise pharmaceutical, veterinary or cosmetic excipients or carriers appropriate for topical administration, including, binders, emollients, skin permeation enhancers, emulsifiers, surfactants, thickening agents, viscosity increasing agents, pH regulators, antioxidants, preservative agents, solvents, dyestuffs, pigments, perfumes or mixtures thereof. The excipients or carriers used have affinity for the skin, are well tolerated, are stable, and are used in an amount suitable to provide the desired consistency and ease of application. The appropriate excipients and/or carriers, and their amounts, can readily be determined by those skilled in the art according to the type of formulation being prepared.

The compositions of the invention may also include liquid carriers such as water, oils including those of petroleum, animal, vegetable or synthetic origin, such as for example peanut oil, soybean oil, mineral oil, sesame oil, castor oil, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, digitonine and the like.

Examples of binders include, without limitation, polyvinyl pyrrolidone, alginates, traganth, and the like. Examples of emollients or skin permeation enhancers include, without limitation, lauryl alcohol, oleyl alcohol, eucalyptol, sodium lauryl sulfate, glyceryl monooleate, sorbitan monooleate, isopropyl myristate, glyceryl myristate, propylene glycol, dimethyl isosorbide, Isopropyl Palmitate, oleic acid, and the like, dimethylsulfoxide, dimethylacetamide, dimethylformamide, surfactants, azone (1-dodecylazacycloheptan-2-one), alcohol, urea, ethoxydiglycol, acetone, polyethylene glycol among others. If desired, the compositions of the invention may be applied in the local areas to be treated by iontophoresis, sonophoresis, electroporation, microelectrical patches, mechanical pressure, osmotic pressure gradient, occlusive cure, microinjections or injections without needles by pressure, as for example oxygen-injections, or any combination thereof, to achieve enhanced penetration of the compound of the invention. The area of application will be determined by the nature of the condition to be treated or prevented.

Examples of emulsifiers or surfactants include, without limitation, polysorbate 80, polysorbate 20, sorbitan groups (spans), lecithin and Potassium Hexadecyl Hydrogen Phosphate, and the like.

Examples of thickening or viscosity increasing agents include, without limitation, synthetic polymers such as carbomers (cross linked polymers of acrylic acid), cellulosic polymers such as hydroxypropyl methylcellulose, methylcellulose, sodium carboxy methylcellulose, and hydroxypropyl cellulose and block copolymers based on ethylene oxide and propylene oxide (pluronic compounds), and the like.

Examples of pH regulators or buffering agents include, without limitation, monobasic sodium phosphate, dibasic sodium phosphate, sodium benzoate, potassium benzoate, sodium citrate, sodium acetate, sodium tartrate, diethanolamine, triethanolamine, sodium hydroxide, citric acid, and the like.

Examples of antioxidant agents include, without limitation, ascorbic acid, sodium ascorbate, sodium bisulfite, sodium sulfite, sodium metabisulfate, curcumin, tetrahydrocurcumin, diacetyl tetrahydrocurcumin, resveratrol, quercetin, hesperidin, myricetin, naringin, alpha-lipoic acid, monothioglycerol, butylated hydroxy anisole (BHA), butylated hydroxy toluene (BHT), propyl gallate, and the like.

Examples of preservatives include, without limitation, methylparaben, methylparaben sodium, propylparaben, propylparaben sodium, benzalkonium chloride, diazolidinyl urea, benzethonium chloride, chlorocresol, thiomarsal, sorbic acid, potassium sorbate and benzyl alcohol, and the like.

Examples of solvents include, without limitation, ethanol, isopropyl alcohol, water, propylene glycol, polyethylene glycol, substituted glycols such as cremophor, or mixtures thereof, and the like.

The compounds of the present invention may also be adsorbed on solid organic polymers or solid mineral supports such as, for example, and without limiting sense tale, bentonite, silica, starch or maltodextrin among others.

As mentioned above, the compounds of the invention are TRPV1 modulators. Some of the compounds of the invention, in particular the compounds of formula (I) wherein $R^3$ is H, are TRPV1 agonists. Some of the compounds of the invention, in particular the compounds of formula (I) wherein $R^3$ is halogen, particularly iodine, are TRPV1 antagonists.

For the purposes of the invention, TRPV1 agonists as defined herein are capable of activating TRPV1 with an $EC_{50}$ value≤10 μM, preferably 1 μM, more preferably ≤500 nM, and TRPV1 antagonists as defined herein are capable of inhibiting TRPV1 with an $IC_{50}$ value≤50 μM, preferably ≤30 μM, more preferably ≤10 μM, where the activation/inhibition of TRPV1 is measured in fluorimetric assays (e.g. in vitro assays) as the ones described in the examples of the present invention.

Thus, the compounds of the invention, via direct desensitization of the receptor in the case of TRPV1 agonists, or by blocking TRPV1 in the case of antagonists, cause a loss of TRPV1 activity. The use of TRPV1 antagonists has the further advantage that they do not cause a burning sensation when applied.

As a consequence, the compounds of the invention are useful in the treatment and/or prevention of conditions or diseases mediated by the inhibition of TRPV1.

Accordingly, the invention also relates to the use of a compound of formula (I) as defined above, including (3,4-dimethoxyphenethylcarbamoyl)methyl but-2-enoate; (3,4-dimethoxy-phenethyl-carbamoyl)methyl 4-methylpentanoate; (3,4-dimethoxybenzylcarbamoyl)methyl 3,3-dimethylbutanoate; (3,4-dimethoxyphenethylcarbamoyl)methyl 3,3-dimethylbutanoate; (3,4-dimethoxyphenethylcarbamoyl)methyl 3-methylbut-2-enoate; (3,4-dimethoxy-benzylcarbamoyl)methyl 4-methylpentanoate; (3,4-dimethoxybenzylcarbamoyl)-methyl 3-methylbut-2-enoate; (2E,4E)-(3,4-dimethoxybenzylcarbamoyl)methyl hexa-2,4-dienoate; (3,4-dimethoxybenzylcarbamoyl)methyl butyrate; (3,4-dimethoxyphenethylcarbamoyl)-methyl butyrate; (3,4-dimethoxyphenethylcarbamoyl)methyl hexa-2,4-dienoate; (3,4-dimethoxyphenethylcarbamoyl)methyl 2-ethylbutanoate; (3,4-dimethoxybenzyl-carbamoyl)methyl but-2-enoate; (3,4-dimethoxybenzylcarbamoyl)methyl but-3-enoate; (3,4-dimethoxybenzylcarbamoyl)methyl but-3-enoate; (3,4-dimethoxybenzyl-carbamoyl)methyl undec-10-enoate; (3,4-dimethoxybenzylcarbamoyl)methyl 2-methylpentanoate; and 2-(3,4-dimethoxyphenethylcarbamoyl)propan-2-yl pentanoate; for the manufacture of a medicament or cosmetic composition for the treatment and/or prevention of conditions or diseases mediated by the inhibition of TRPV1.

It also forms part of the invention a method for the treatment and/or prevention of conditions or diseases mediated by the inhibition of TRPV1, comprising administering an effective amount of the compound of formula (I) as defined above, including (3,4-dimethoxyphenethylcarbamoyl)methyl but-2-enoate; (3,4-dimethoxy-phenethyl-carbamoyl)methyl 4-methylpentanoate; (3,4-dimethoxybenzylcarbamoyl)methyl 3,3-dimethylbutanoate; (3,4-dimethoxyphenethylcarbamoyl)methyl 3,3-dimethylbutanoate; (3,4-dimethoxyphenethylcarbamoyl)methyl 3-methylbut-2-enoate; (3,4-dimethoxybenzylcarbamoyl)methyl 4-methylpentanoate; (3,4-dimethoxybenzylcarbamoyl)-methyl 3-methylbut-2-enoate;

(2E,4E)-(3,4-dimethoxybenzylcarbamoyl)methyl hexa-2,4-dienoate; (3,4-dimethoxybenzylcarbamoyl)methyl butyrate; (3,4-dimethoxyphenethylcarbamoyl)-methyl butyrate; (3,4-dimethoxyphenethylcarbamoyl)methyl hexa-2,4-dienoate; (3,4-dimethoxyphenethylcarbamoyl)methyl 2-ethylbutanoate; (3,4-dimethoxybenzyl-carbamoyl)methyl but-2-enoate; (3,4-dimethoxybenzylcarbamoyl)methyl but-3-enoate; (3,4-dimethoxybenzylcarbamoyl)methyl but-3-enoate; (3,4-dimethoxybenzyl-carbamoyl)methyl undec-10-enoate; (3,4-dimethoxybenzylcarbamoyl)methyl 2-methylpentanoate; and 2-(3,4-dimethoxyphenethylcarbamoyl)propan-2-ylpentanoate; and one or more pharmaceutically, veterinary or cosmetically acceptable excipients or carriers, in a subject in need thereof, including a human.

In one embodiment of the invention, optionally in combination with one or more features of the various embodiments described above or below, the conditions or diseases mediated by the inhibition of TRPV1 are selected from pain, inflammation and cancer.

The antitumor activity of TRPV1 is for example disclosed in Breast Cancer 2016 13, 8, pp. 243-252, and Nat. Rev. Drug Discov. 2011, 10(8), pp. 601-20.

The inhibition of TRPV1 has also been related to relief of pain and decrease of inflammation. For example in J. Pain 2006, 7(10), pp. 735-46, it is disclosed that potent TRPV1 noncompetitive antagonist exhibits anti-inflammatory and analgesic activity in preclinical models of acute and chronic pain. In the context of the invention pain can be associated to post-herpetic neuralgia, shingles (herpes zoster), diabetic neuropathy, postmastectomy pain syndrome, oral neuropathic pain, trigeminal neuralgia, temperomandibular joint disorders, cluster headache, osteoarthritis, arthritis pain, rhinopathy, oral mucositis, cutaneous allergy, detrusor hyperreflexia, loin pain/hematuria syndrome, neck pain, back pain, amputation stump pain, reflex sympathetic dystrophy and pain due to skin tumor.

Inhibition of TRPV1 can also be a therapeutic target in certain skin diseases, such as sensitive skin, itch (pruritus), rosacea, acne vulgaris, atopic dermatitis, psoriasis and psoriatic arthritis.

Sensitive skin is a skin condition in which skin is prone to itching and irritation experienced as a subjective sensation when using cosmetics and toiletries. In Exp. Dermatol. 2010, 19(11), pp. 980-6, it is disclosed the inhibition of TRPV1 by a TRPV1 antagonist for the treatment of sensitive skin.

Itch (pruritus) can be defined as an unpleasant cutaneous sensation associated with urge desire to scratch. In Journal of Dermatological Science 2012, 65, pp. 81-85, it is disclosed that the discovery of increased TRPV1 expression in nerve fibers in aged skin suggests an important role of TRPV1 in the pathophysiology of the skin symptom related to aging, such as pruritus.

Rosacea is a long term skin condition characterized by facial redness, small and superficial dilated blood vessels on facial skin, papules, pustules, and swelling. It has been disclosed that in affected skin of patients with various types of rosacea, altered expression patterns for TRPV1 were identified; this suggesting the possible involvement of TRPV1 in the pathogenesis of rosacea (Br. J. Pharmacol. 2014, 171(10), pp. 2568-2581).

Psoriasis is a long-lasting autoimmune disease that is characterized by patches of abnormal skin, which are typically red, itchy, and scaly. Acne vulgaris is a long-term skin disease that occurs when hair follicles are clogged with dead skin cells and oil from the skin and is characterized by blackheads or whiteheads, pimples, greasy skin, and possible scarring. Atopic dermatitis is a type of inflammation of the skin (dermatitis). It results in itchy, red, swollen, and cracked skin. Psoriatic arthritis is a long-term inflammatory arthritis that occurs in people affected by the autoimmune disease psoriasis. The classic feature of psoriatic arthritis is swelling of entire fingers and toes.

The role of TRPV1 in the above diseases and/or conditions is for example described in Arthritis Res Ther 2014, 16(5), 470; J Invest Dermatol. 2009, 129(2), pp. 329-39; and J Invest Dermatol. 2011, 131(7), pp. 1576-9.

Thus, in another embodiment of the invention, optionally in combination with one or more features of the various embodiments described above or below, the conditions or diseases mediated by the inhibition of TRPV1 are selected from sensitive skin, itch (pruritus), rosacea, acne vulgaris, atopic dermatitis, psoriasis and psoriatic arthritis.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

EXAMPLES

The following abbreviations have been used in the examples:
TBDMSCI: tert-Butyldimethylsilyl chloride
TEA: Triethylamine Example 1

Synthesis of N-(4-hydroxy-3-methoxybenzyl)formamide (Intermediate 1)

The (4-hydroxy-3-methoxyphenyl)methanaminium chloride (2.30 g, 15 mmol) is solubilized in aqueous saturated $Na_2CO_3$ solution and extracted with THF (×3). The collected organic layers are evaporated. 4-(aminomethyl)-2-methoxyphenol is then solubilized in THF (70 mL) and methyl formate (1.12 mL, 18 mmol) is added. The reaction is stirred overnight at room temperature. Then, 1.8 eq of methyl formate (1.68 mL, 27 mmol) is added and the reaction is stirred for additional 6 hours. Removal of volatile under vacuo yielded intermediate 1 as a brown oil (2.61 g, 14.4 mmol, 96%). Analytical data: $^1$H-NMR (300 MHz, $CDCl_3$): δ 8.87 (s, 1H), 8.38 (br s, 1H), 8.08 (s, 1H), 6.82 (s, 1H), 6.72-6.64 (m, 2H), 4.17 (d, J 5.8 Hz, 2H), 3.73 (s, 3H). MS: M+1 182

Example 2

Synthesis of N-(4-((tert-butyldimethylsilyl)oxy)-3-methoxybenzyl)formamide (Intermediate 2)

To a solution of N-(4-hydroxy-3-methoxybenzyl)formamide (3.29 g, 18.17 mmol) in dry DMF (35 mL) are added in order TBDMSCI (3.29 g, 21.80 mmol), N,N-dimethylaminopyridine (44 mg, 0.36 mmol) and imidazole (1.36 g, 19.99 mmol) under nitrogen. The reaction is stirred at room temperature for 2 hours, then is washed with water (×1) and extracted with diethyl ether (×1). The organic layer is dried over sodium sulfate and the volatile is removed under vacuo. The crude material, after purification by column chromatography using petroleum ether/ethyl acetate 6:4 and then petroleum ether/ethyl acetate 4:6 as eluent, yielded intermediate 2 (2.90 g, 9.83 mmol, 54%) as a dark yellow oil. Analytical data: $^1$H-NMR (300 MHz, CDCl$_3$): δ 8.04 (s, 1H), 6.92 (br s, 1H), 6.68 (d, J 8.0 Hz, 1H), 6.65 (d, J 1.9 Hz, 1H), 6.60 (dd, J 8.0, 1.9 Hz, 1H), 4.22 (d, J 6.1 Hz, 2H), 3.66 (s, 3H), 0.91 (s, 9H), 0.06 (s, 6H). MS: M+1 296

Example 3

Synthesis of tert-butyl(4-(isocyanomethyl)-2-methoxyphenoxy)dimethylsilane (Intermediate 3)

N-(4-((tert-butyldimethylsilyl)oxy)-3-methoxybenzyl)formamide (200 mg, 0.68 mmol) is dissolved in dry CH$_2$Cl$_2$ (2 mL) at 0° C. and TEA (343 mg, 3.39 mmol) is added under nitrogen. A solution of POCl$_3$ (93 μL, 1 mmol) in dry CH$_2$Cl$_2$ (2 mL) is added dropwise and the reaction is stirred for 1 hour. Aqueous saturated NaHCO$_3$ solution is then added and the mixture is stirred for 10 minutes. Then, the reaction is extracted with CH$_2$Cl$_2$, dried over sodium sulfate and evaporated. The crude material is purified by column chromatography using petroleum ether/ethyl acetate 4:6 as eluent, yielding intermediate 3 (164 mg, 0.59 mmol, 87%) as a dark yellow oil. Analytical data: $^1$H-NMR (300 MHz, CDCl$_3$): δ 6.83-6.73 (m, 3H), 4.52 (s, 2H), 3.78 (s, 3H), 0.97 (s, 9H), 0.13 (s, 6H). MS: M+1 279

Example 4

Synthesis of N-(4-((tert-butyldimethylsilyl)oxy)-2-iodo-5-methoxybenzyl)-formamide (Intermediate 4)

To a solution of N-(4-((tert-butyldimethylsilyl)oxy)-3-methoxybenzyl)formamide (1.65 g, 5.59 mmol) in CHCl$_3$ (17 mL) silver trifluoroacetate (1.23 g, 5.59 mmol) and a solution of iodine (1.42 g, 5.59 mmol) in CHCl$_3$ (14 mL) are added. The reaction is stirred for 1 hour and filtered under vacuo over a pad of celite. The filtrate is diluted with CH$_2$Cl$_2$, washed with aqueous saturated solution of NaHCO$_3$ (×1) and with aqueous saturated Na$_2$S$_2$O$_3$ solution (×1). The organic layer is dried over sodium sulfate and evaporated to give a yellow solid (1.98 g, 4.70 mmol, 84%). Analytical data: $^1$H-NMR (300 MHz, CDCl$_3$): δ 8.12 (s, 1H), 7.16 (s, 1H), 6.78 (s, 1H), 6.74 (br t, 1H), 4.31 (d, J 6.0 Hz, 2H), 0.91 (s, 9H), 0.07 (s, 6H). MS: M+1 422

Example 5

Synthesis of tert-butyl(5-iodo-4-(isocyanomethyl)-2-methoxyphenoxy)-dimethylsilane (Intermediate 5)

This intermediate was prepared by the process as described in example 3 but using N-(4-((tert-butyldimethylsilyl)oxy)-2-iodo-5-methoxybenzyl)formamide as starting material. A yellow solid was obtained (84%). Analytical data: $^1$H-NMR (300 MHz, CDCl$_3$): δ 7.25 (s, 1H), 6.96 (s, 1H), 4.52 (s, 2H), 3.79 (s, 3H), 0.96 (s, 9H), 0.14 (s, 6H). MS: M+1 404

Example 6

Synthesis of (3,4-bis((tert-butyldimethylsilyl)oxy)phenyl)methanamine (Intermediate 6)

To a solution of (3,4-dihydroxyphenyl)methanaminium bromide (4.50 g, 20.44 mmol) and imidazole (4.18 g, 61.33 mmol) in dry CH$_2$Cl$_2$ (50 mL) a solution of TBDMSCI (6.16 g, 40.89 mmol) in dry CH$_2$Cl$_2$ (25 mL) is added dropwise under nitrogen. The reaction is stirred at room temperature overnight. The volatile is evaporated under reduced pressure. Ethyl acetate is added and the organic phase is washed with water (×4), dried over sodium sulfate and evaporated. The crude material is purified by column chromatography using petroleum ether/ethyl acetate 2:8 and then ethyl acetate/methanol 8:2 as eluent, yielding intermediate 6 (5.69 g, 14.37 mmol, 76%) as a dark yellow oil. Analytical data: $^1$H-NMR (300 MHz; CDCl$_3$): δ 6.79-6.76 (m, 3H), 3.78 (s, 2H), 1.01-0.93 (m, 18H), 0.19-0.15 (m, 12H). MS: M+1 369

Example 7

Synthesis of N-(3,4-bis((tert-butyldimethylsilyl)oxy)benzyl)formamide (Intermediate 7)

A solution of (3,4-bis((tert-butyldimethylsilyl)oxy)phenyl)methanamine (4.95 g, 13.47 mmol) in ethyl formate (50 mL) is heated at reflux for 28 h. The volatile is removed under vacuo, yielding intermediate 7 (5.17 g, 13.06 mmol, 97%) as a deep yellow oil. Analytical data: $^1$H-NMR (300 MHz; CDCl$_3$): refer to the main rotamer; δ 8.22 (s, 1H), 6.78-6.72 (m, 3H), 4.34 (d, J 3.2 Hz, 2H), 0.97-0.87 (m, 18H), 0.21-0.18 (m, 12H). MS: M+1 397

Example 8

Synthesis of ((4-(isocyanomethyl)-1,2-phenylene)bis(oxy))bis(tert-butyldimethylsilane) (Intermediate 8)

This intermediate was prepared by the process as described in example 3 but using N-(3,4-bis((tert-butyldimethylsilyl)oxy)benzyl)formamide as starting material. A yellow solid was obtained (61%).
Analytical data: $^1$H-NMR (300 MHz, CDCl$_3$): δ 6.83-6.81 (m, 2H), 6.76 (d, J 8.2 Hz, 1H), 4.50 (s, 2H), 1.04-0.92 (m, 18H), 0.26-0.19 (m, 12H).

Example 9

Synthesis of N-(4,5-bis((tert-butyldimethylsilyl)oxy)-2-iodobenzyl)formamide (Intermediate 9)

This intermediate was prepared by the process as described in example 4 but using N-(3,4-bis((tert-butyldimethylsilyl)oxy)benzyl)formamide as starting material. An amorphous orange solid was obtained (66%).
Analytical data: $^1$H-NMR (300 MHz, CDCl$_3$): refer to the main rotamer; δ 8.22 (s, 1H), 7.23 (s, 1H), 6.89 (s, 1H), 5.90 (br s, 1H), 4.39 (d, J 6.1 Hz, 2H), 1.04-0.90 (m, 18H), 0.24-0.18 (m, 12H). MS: M+1 523

Example 10

Synthesis of ((4-iodo-5-(isocyanomethyl)-1,2-phenylene)bis(oxy))bis(tert-butyldimethylsilane) (Intermediate 10)

This intermediate was prepared by the process as described in example 3 but using N-(4,5-bis((tert-butyldimethylsilyl)oxy)-2-iodobenzyl)formamide as starting material. A deep yellow solid was obtained (87%).

Analytical data: $^1$H-NMR (300 MHz; CDCl$_3$): δ 7.28 (s, 1H), 7.03 (s, 1H), 4.54 (s, 2H), 1.08-0.98 (m, 18H), 0.22-0.19 (m, 12H).

Example 11

Synthesis of 2-(3,4-bis((tert-butyldimethylsilyl)oxy)phenyl)ethanamine (Intermediate 11)

This intermediate was prepared by the process as described in example 6 but using 2-(3,4-dihydroxyphenyl)ethanaminium chloride as starting material. A white solid was obtained (59%).

Analytical data: $^1$H-NMR (300 MHz, CDCl$_3$): δ 8.34 (br s, 2H), 6.74-6.67 (m, 3H), 3.19 (t, J 6.8 Hz, 2H), 2.99 (t, J 6.8 Hz, 2H), 1.04-0.76 (m, 18H), 0.25-0.17 (m, 12H). MS: M+1 383

Example 12

Synthesis of N-(3,4-bis((tert-butyldimethylsilyl)oxy)phenethyl)formamide (Intermediate 12)

2-(3,4-bis((tert-butyldimethylsilyl)oxy)phenyl)ethanamine (2.72 g, 7.14 mmol) was dissolved in a solution of 1:1 methyl formate and methanol (115 mL) under nitrogen. K$_2$CO$_3$ (9.87 g, 71.39 mmol) is added to the above mixture and the reaction is stirred at reflux for 2 h. Then, the reaction is filtered and, after evaporation of the volatile, water is added. The aqueous layer is extracted with CH$_2$Cl$_2$ (×2) and the organic phase is dried over sodium sulfate and evaporated under vacuo, yielded a pale yellow oil (2.55 g, 6.22 mmol, 87%).

Analytical data: $^1$H-NMR (300 MHz, CDCl$_3$): refer to the main rotamer; δ 8.12 (s, 1H), 6.76 (d, J 3.1 Hz, 1H), 6.64-6.61 (m, 2H), 5.48 (br s, 1H), 3.51 (q, J 6.3 Hz, 2H), 2.70 (t, J 6.3 Hz, 2H), 1.02-0.98 (m, 18H), 0.26-0.14 (m, 12H). MS: M+1 411

Example 13

Synthesis of ((4-(2-isocyanoethyl)-1,2-phenylene)bis(oxy))bis(tert-butyldimethylsilane) (Intermediate 13)

This intermediate was prepared by the process as described in example 3 but using N-(3,4-bis((tert-butyldimethylsilyl)oxy)phenethyl)formamide as starting material. A pale yellow oil was obtained (77%).

Analytical data: $^1$H-NMR (300 MHz, CDCl$_3$): δ 6.78 (d, J 3.1 Hz, 1H), 6.69-6.67 (m, 2H), 3.54 (t, J 6.2 Hz, 2H), 2.86 (t, J 6.2 Hz, 2H), 1.00-0.99 (m, 18H), 0.24-0.20 (m, 12H).

Example 14

Synthesis of N-(4,5-bis((tert-butyldimethylsilyl)oxy)-2-iodophenethyl)-formamide (Intermediate 14)

This intermediate was prepared by the process as described in example 4 but using N-(3,4-bis((tert-butyldimethylsilyl)oxy)phenethyl)formamide as starting material. A deep yellow oil was obtained (86%).

Analytical data: $^1$H-NMR (300 MHz, CDCl$_3$): refer to the main rotamer; δ 8.15 (s, 1H), 7.25 (s, 1H), 6.67 (s, 1H), 5.58 (br s, 1H), 3.50 (q, J 6.2 Hz, 2H), 2.82 (t, J 6.2 Hz, 2H), 1.07-0.90 (m, 18H), 1.18-0.08 (m, 12H). MS: M+1 537

Example 15

Synthesis of ((4-iodo-5-(2-isocyanoethyl)-1,2-phenylene)bis(oxy))bis(tert-butyldimethylsilane) (Intermediate 15)

This intermediate was prepared by the process as described in example 3 but using N-(4,5-bis((tert-butyldimethylsilyl)oxy)-2-iodophenethyl)formamide as starting material. A white solid was obtained (82%).

Analytical data: $^1$H-NMR (300 MHz, CDCl$_3$): δ 7.25 (s, 1H), 6.77 (s, 1H), 3.57 (t, J 6.1 Hz, 2H), 2.96 (t, J 6.1 Hz, 2H), 1.03-0.93 (m, 18H), 0.21-0.19 (m, 12H).

Example 16

Synthesis of 2-((4-hydroxy-3-methoxybenzyl)amino)-2-oxoethyl butyrate

To a solution of tert-butyl(4-(isocyanomethyl)-2-methoxyphenoxy)dimethylsilane (Intermediate 3) (200 mg, 0.72 mmol) in CH$_2$Cl$_2$ (6.2 mL) 37% aqueous formaldehyde solution (215 μL, 2.88 mmol) and butyric acid (the compound R$^5$—COOH in scheme 1) (63 mg, 0.72 mmol) are added and the resulting mixture is stirred at reflux for 3 h and then is left to reach room temperature and stirred overnight. Then, the volatile is removed under vacuo and the product is solubilized in THF (2 mL) and cooled down to 0° C. At this temperature, acetic acid (49 μL, 0.86 mmol) and TBAF (0.86 mL, 0.86 mmol) are added. The reaction is stirred for 30 minutes. The volatile is evaporated and ethyl acetate is added, washed with water (×1) and with aqueous saturated NaHCO$_3$ solution (×1). The collected organic layers were dried over sodium sulfate and evaporated. Purification by column chromatography using petroleum ether/ethyl acetate 9:1 and then petroleum ether/ethyl acetate 6:4 as eluent yielded compound 16 as a yellowish solid. (120 mg, 0.43 mmol, 59%)

Analytical data: $^1$H-NMR (300 MHz, CDCl$_3$): δ 6.85-6.65 (m, 3H), 6.59 (br t, 1H), 6.14 (br s, 1H), 4.54 (s, 2H), 4.33 (d, J 5.8 Hz, 2H), 3.80 (s, 3H), 2.31 (t, J 7.4 Hz, 2H), 1.60 (m, J 7.4 Hz, 2H), 0.89 (t, J 7.4 Hz, 3H). MS: M+1 280.

Following the same synthetic route for example 16 and using the same reagents and intermediates unless otherwise indicated in the table below, the following compounds were obtained:

| Example | Yield | Reagents | $^1$H-NMR (300 MHz, CDCl$_3$, δ) |
|---|---|---|---|
| 17<br>2-((4-hydroxy-2-iodo-5-methoxybenzyl)amino)- | 60% | Intermediate 5 (example 5) and butyric acid | 7.35 (s, 1H), 6.93 (s, 1H), 4.58 (s, 2H), 4.45 (d, J 5.8 Hz, 2H), 3.88 |

-continued

| Example | Yield | Reagents | ¹H-NMR (300 MHz, CDCl₃, δ) |
|---|---|---|---|
| 2-oxoethyl butyrate | | ($R_6$—COOH) | (s, 3H), 2.39 (t, J 7.4 Hz, 2H), 1.80-1.60 (m, J 7.4 Hz, 2H), 0.96 (t, J 7.4 Hz, 3H). MS: M − 1 407 |
| 18 2-((4-hydroxy-3-methoxybenzyl)amino)-2-oxoethyl pentanoate | 60% | Intermediate 3 (example 3) and pentanoic acid ($R_6$—COOH) | 6.80-6.60 (m, 3H), 6.31 (br t, 1H), 4.52 (s, 2H), 4.31 (d, J 5.5 Hz, 2H), 3.77 (s, 3H), 2.32 (t, J 7.4 Hz, 2H), 1.54 (quint, J 7.4 Hz, 2H), 1.26 (m, J 7.4 Hz, 2H), 0.83 (t, J 7.4 Hz, 3H). MS: M + 1 296 |
| 19 2-((4-hydroxy-2-iodo-5-methoxybenzyl)amino)-2-oxoethyl pentanoate | 51% | Intermediate 5 (example 5) and pentanoic acid ($R_6$—COOH) | 7.21 (s, 1H), 6.87 (s, 1H), 4.57 (d, J 8.8 Hz, 2H), 4.32 (s, 2H), 3.83 (s, 3H), 2.43 (t, J 7.2 Hz, 2H), 1.60 (quint, J 7.2 Hz, 2H), 1.34 (m, J 7.2 Hz, 2H), 0.90 (t, J 7.2 Hz, 3H). MS: M + 1 420 |
| 20 2-((4-hydroxy-3-methoxybenzyl)amino)-2-oxoethyl 3-methylbutanoate | 65% | Intermediate 3 (example 3) and 3-methyl-butanoic acid ($R_6$—COOH) | 6.80-6.65 (m, 4H), 4.53 (s, 2H), 4.32 (d, J 5.8 Hz, 2H), 3.78 (s, 3H), 2.20 (d, J 6.9 Hz, 2H), 2.03 (m, J 6.9 Hz, 1H), 0.91 (d, J 6.9 Hz, 6H). MS: M + 1 296 |
| 21 2-((4-hydroxy-2-iodo-5-methoxybenzyl)amino)-2-oxoethyl 3-methylbutanoate | 75% | Intermediate 5 (example 5) and 3-methyl-butanoic acid ($R_6$—COOH) | 7.26 (s, 1H), 6.84 (s, 1H), 6.76 (br, t, J 6.1 Hz, 1H), 4.55 (s, 2H), 4.38 (d, J 6.1 Hz, 2H), 3.77 (s, 3H), 2.25 (d, J 6.6 Hz, 2H), 2.1 (m, J 6.6 Hz, 1H), 0.91 (d, J 6.6 Hz, 6H). MS: M − 1 420 |
| 22 2-((4-hydroxy-3-methoxybenzyl)amino)-2-oxoethyl hexanoate | 35% | Intermediate 3 (example 3) and hexanoic acid ($R_6$—COOH) | 6.83 (d, J 8.0 Hz, 1H), 6.78 (d, J 1.6 Hz, 1H), 6.73 (dd, J 8.0, 1.6 Hz, 1H), 6.43 (br t, 1H), 4.57 (s, 2H), 4.37 (d, J 5.8 Hz, 2H), 3.84 (s, 3H), 2.35 (t, J 7.4 Hz, 2H), 1.59 (quint, J 7.4 Hz, 2H), 1.28-1.24 (m, 4H), 0.85 (t, J 6.9 Hz, 3H). MS: M + 1 310 |
| 23 2-((4-hydroxy-2-iodo-5-methoxybenzyl)amino)-2-oxoethyl hexanoate | 100% | Intermediate 5 (example 5) and hexanoic acid ($R_6$—COOH) | 7.31 (s, 1H), 6.89 (s, 1H), 6.75 (br t, 1H), 4.58 (s, 2H), 4.43 (d, J 5.8 Hz, 2H), 3.81 (s, 3H), 2.38 (t, J 7.4 Hz, 2H), 1.60 (quint, J 7.4 Hz, 2H), 1.30-1.25 (m, 4H), 0.85 (t, J 6.9 Hz, 3H). MS: M − 1 434 |
| 24 (2E,4E)-2-((4-hydroxy-3-methoxybenzyl)amino)-2-oxoethyl hexa-2,4-dienoate | 65% | Intermediate 3 (example 3) and (2E,4E)-hexa-2,4-dienoic acid ($R_6$—COOH) | 7.23 (m, 1H), 6.77 (d, J 7.9 Hz, 1H), 6.73 (d, J 1.7 Hz, 1H), 6.71-6.70 (m, 2H), 6.11 (m, 2H), 5.74 (d, J 15.0 Hz, 1H), 4.60 (s, 2H), 4.33 (d, J 5.8 H, 2H), 3.78 (s, 3H), 1.79 (d, J 4.7 Hz, 3H). MS: M − 1 304 |
| 25 (2E,4E)-2-((4-hydroxy-2-iodo-5-methoxybenzyl)-amino)-2-oxoethyl hexa-2,4-dienoate | 47% | Intermediate 5 (example 5) and (2E,4E)-hexa-2,4-dienoic acid ($R_6$—COOH) | 9.39 (br s, 1H), 8.52 (br t, J 4.7 Hz, 1H), 7.35-7.20 (m, 1H), 7.18 (s, 1H), 6.82 (s, 1H), 6.40-6.20 (m, 2H), 5.95 (d, J 15.4 Hz, 1H), 4.60 (s, 2H), 4.14 (d, J 4.7 Hz, 2H), 3.74 (s, 3H), 1.83 (d, J 3.8 Hz, 3H). MS: M − 1 430 |
| 26 2-((4-hydroxy-3-methoxy-benzyl)amino)- | 60% | Intermediate 3 (example 3) and heptanoic acid | 6.90-6.68 (m, 3H), 6.51 (br t, 1H), 4.56 (s, 2H), 4.36 (d, J 5.5 Hz, 2H), |

| Example | Yield | Reagents | $^1$H-NMR (300 MHz, CDCl$_3$, δ) |
|---|---|---|---|
| 2-oxoethyl heptanoate | | (R$_6$—COOH) | 3.83 (s, 3H), 2.34 (t, J 7.4 Hz, 2H), 1.58 (quint, J 7.4 Hz, 2H), 1.40-1.10 (m, 6H), 0.83 (t, J 6.6 Hz, 3H). MS: M + 1 324 |
| 27 2-((4-hydroxy-2-iodo-5-methoxybenzyl)amino)-2-oxoethyl heptanoate | 77% | Intermediate 5 (example 5) and heptanoic acid (R$_6$—COOH) | 7.30 (s, 1H), 6.88 (s, 1H), 6.73 (br t, 1H), 4.57 (s, 2H), 4.42 (d, J 5.8 Hz, 2H), 3.82 (s, 3H), 2.38 (t, J 7.7 Hz, 2H), 1.62 (quint, J 7.7 Hz, 2H), 1.40-1.15 (m, 6H), 0.85 (t, J 6.6 Hz, 3H). MS: M − 1 448 |
| 28 2-((4-hydroxy-3-methoxy-benzyl)amino)-2-oxoethyl octanoate | 57% | Intermediate 3 (example 3) and octanoic acid (R$_6$—COOH) | 6.73-6.65 (m, 4H), 4.50 (s, 2H), 4.28 (d, J 5.5 Hz, 2H), 3.74 (s, 3H), 2.29 (t, J 7.2 Hz, 2H), 1.53 (quint, J 7.2 Hz, 2H), 1.30-1.12 (m, 8H), 0.80 (t, J 4.4 Hz, 3H). MS: M + 1 339 |
| 29 2-((4-hydroxy-2-iodo-5-methoxybenzyl)amino)-2-oxoethyl octanoate | 52% | Intermediate 5 (example 5) and octanoic acid (R$_6$—COOH) | 7.32 (s, 1H), 6.90 (s, 1H), 6.67 (br t, 1H), 5.89 (br s, 1H), 4.57 (s, 2H), 4.43 (d, J 6.1 Hz, 2H), 3.85 (s, 3H), 2.39 (t, J 7.4 Hz, 2H), 1.63 (quint, J 7.4 Hz, 2H), 1.40-1.15 (m, 8H), 0.86 (t, J 6.0 Hz, 3H). MS: M + 1 464 |
| 30 2-((4-hydroxy-3-methoxybenzyl)amino)-2-oxoethyl nonanoate. | 32% | Intermediate 3 (example 3) and nonanoic acid (R$_6$—COOH) | 6.78 (d, J 8.0, 1H), 6.73 (s, 1H), 6.67 (d, J 8.0 Hz, 1H), 6.62 (br t, 1H), 4.53 (s, 2H), 4.32 (d, J 5.5 Hz, 2H), 3.79 (s, 3H), 2.32 (t, J 7.7 Hz, 2H), 1.58-1.53 (m, 2H), 1.20-1.14 (m, 10H), 0.82 (t, 3H). MS: M + 1 353 |
| 31 2-((4-hydroxy-2-iodo-5-methoxybenzyl)amino)-2-oxoethyl nonanoate | 93% | Intermediate 5 (example 5) and nonanoic acid (R$_6$—COOH) | 7.30 (s, 1H), 6.88 (s, 1H), 6.71 (br t, 1H), 4.56 (s, 2H), 4.41 (d, J 6.3 Hz, 2H), 3.81 (s, 3H), 2.38 (t, J 7.3 Hz, 2H), 1.62 (quint, J 7.3 Hz, 2H), 1.25-1.18 (m, 10H), 0.85 (t, J 7.1 Hz, 3H). MS: M − 1 476 |
| 32 (E)-2-((4-hydroxy-3-methoxybenzyl)amino)-2-oxoethyl 3,7-dimethylocta-2,6-dienoate | 73% | Intermediate 3 (example 3) and (E)-3,7-dimethylocta-2,6-dienoic acid (R$_6$—COOH) | 6.79 (d, J 8.0 Hz, 1H), 6.75 (s, 1H), 6.70 (d, J 8.0 Hz, 1H), 6.61 (br t, 2H), 5.67 (s, 1H), 5.00 (br t, 1H), 4.57 (s, 2H), 4.35 (d, J 6.1 Hz, 2H), 3.80 (s, 3H), 2.11 (m, 7H), 1.62 (s, 3H), 1.55 (s, 3H). MS: M − 1 360 |
| 33 (E)-2-((4-hydroxy-2-iodo-5-methoxybenzyl)-amino)-2-oxoethyl 3,7-dimethylocta-2,6-dienoate | 66% | Intermediate 5 (example 5) and (E)-3,7-dimethylocta-2,6-dienoic acid (R$_6$—COOH) | 6.87-6.72 (m, 2H), 6.50 (br t, 1H), 5.01 (br s, 1H), 4.90-4.80 (m, 1H), 4.57 (s, 2H), 4.38 (d, J 4.1 Hz, 2H), 3.75 (s, 3H), 2.20-2.00 (m, 7H), 1.63 (s, 3H), 1.55 (s, 3H). MS: M + 1 486 |
| 34 2-((4-hydroxy-3-methoxybenzyl)amino)-2-oxoethyl decanoate | 62% | Intermediate 3 (example 3) and decanoic acid (R$_6$—COOH) | 6.77-6.64 (m, 4H), 4.51 (s, 2H), 4.30 (d, J 5.5 Hz, 2H), 3.76 (s, 3H), 2.31 (t, J 7.4 Hz, 2H), 1.54 (quint, J 7.4 Hz, 2H), 1.30-1.12 (m, 12H), 0.81 (t, J 6.3 Hz, 3H). MS: M + 1 366 |
| 35 2-((4-hydroxy-2-iodo-5- | 69% | Intermediate 5 (example 5) and | 7.28 (s, 1H), 6.86 (s, 1H), 6.75 (br t, 1H), |

| Example | Yield | Reagents | ¹H-NMR (300 MHz, CDCl₃, δ) |
|---|---|---|---|
| methoxybenzyl)amino)-2-oxoethyl decanoate | | decanoic acid ($R_6$—COOH) | 4.56 (s, 2H), 4.41 (d, J 6.1 Hz, 2H), 3.80 (s, 3H), 2.38 (t, J 7.4 Hz, 2H), 1.62 (quint, J 7.4 Hz, 2H), 1.35-1.15 (m, 12H), 0.85 (t, J 6.6 Hz, 3H). MS: M − 1 490 |
| 36 2-((4-hydroxy-3-methoxybenzyl)amino)-2-oxoethyl dodecanoate | 98% | Intermediate 3 (example 3) and dodecanoic acid ($R_6$—COOH) | 6.80 (d, J 8.0 Hz, 1H), 6.75 (s, 1H), 6.70 (d, J 8.0 Hz, 1H), 6.55 (br t, 1H), 4.54 (s, 2H), 4.34 (d, J 5.8, 2H), 3.81 (s, 3H), 2.33 (t, J 7.3 Hz, 2H), 1.57 (quint, J 7.3 Hz, 2H), 1.21-1.17 (m, 16H), 0.84 (t, J 7.1 Hz, 3H). MS: M − 1 392 |
| 37 2-((4-hydroxy-2-iodo-5-methoxybenzyl)-amino)-2-oxoethyl dodecanoate | 70% | Intermediate 5 (example 5) and dodecanoic acid ($R_6$—COOH) | 7.29 (s, 1H), 6.88 (s, 1H), 6.75 (br t, J 6.0 Hz, 1H), 4.56 (s, 2H), 4.41 (d, J 6.1 Hz, 2H), 3.83 (s, 3H), 2.38 (t, J 7.4 Hz, 2H), 1.62 (quint, J 7.4 Hz, 2H), 1.38-1.18 (m, 16H), 0.85 (t, J 6.1 Hz, 3H). MS: M − 1 518 |
| 38 2-((4-hydroxy-3-methoxybenzyl)amino)-2-oxoethyl pentadecanoate | 73% | Intermediate 3 (example 3) and pentadecanoic acid ($R_6$—COOH) | 6.84 (d, J 8.0 Hz, 1H), 6.78 (d, J 1.9 Hz, 1H), 6.75 (dd, J 8.0, 1.9 Hz, 1H), 6.41 (br t, 1H), 4.57 (s, 2H), 4.38 (d, J 5.8 Hz, 2H), 3.85 (s, 3H), 2.35 (t, J 7.3 Hz, 2H), 1.59 (quint, J 7.3 Hz, 2H), 1.23-1.18 (m, 22H), 0.86 (t, J 6.9 Hz, 3H). MS: M − 1 434 |
| 39 2-((4-hydroxy-2-iodo-5-methoxybenzyl)amino)-2-oxoethyl pentadecanoate | 82% | Intermediate 5 (example 5) and pentadecanoic acid ($R_6$—COOH) | 7.31 (s, 1H), 6.90 (s, 1H), 6.67 (br t, 1H), 4.56 (s, 2H), 4.43 (d, J 6.1 Hz, 2H), 3.84 (s, 3H), 2.38 (t, J 7.2 Hz, 2H), 1.63 (br quint, J 7.2 Hz, 2H), 1.26-1.19 (m, 22H), 0.86 (t, J 6.8 Hz, 3H). MS: M − 1 560 |
| 40 2-((4-hydroxy-3-methoxybenzyl)amino)-2-oxoethyl stearate | 24% | Intermediate 3 (example 3) and octadecanoic acid ($R_6$—COOH) | 6.86 (d, J 8.0 Hz, 1H), 6.80 (d, J 1.6 Hz, 1H), 6.75 (dd, J 8.0, 1.6 Hz, 1H), 6.32 (br t, 1H), 4.59 (s, 2H), 4.40 (d, J 2.9 Hz, 2H), 3.87 (s, 3H), 2.36 (t, J 7.5 Hz, 2H), 1.27-1.15 (m, 33H). MS: M − 1 476 |
| 41 2-((4-hydroxy-2-iodo-5-methoxybenzyl)amino)-2-oxoethyl stearate | 90% | Intermediate 5 (example 5) and octadecanoic acid ($R_6$—COOH) | 7.34 (s, 1H), 6.91 (s, 1H), 6.66 (br t, 1H), 4.57 (s, 1H), 4.44 (d, J 4.7 Hz, 2H), 3.86 (s, 3H), 2.39 (t, J 7.5 Hz, 3H), 1.64 (quint, J 7.5 Hz, 2H), 1.40-1.10 (m, 28H), 0.87 (t, J 4.7 Hz, 3H). MS: M − 1 602 |
| 42 2-((4-hydroxy-2-iodo-5-methoxybenzyl)amino)-2-oxoethyl oleate | 37% | Intermediate 3 (example 3) and (9Z)-octadec-9-enoic acid ($R_6$—COOH) | 6.80 (d, J 8.2 Hz, 1H), 6.76 (d, J 1.6 Hz, 1H), 6.70 (dd, J 8.2, 1.6 Hz, 1H), 6.51 (br t, 1H), 5.31 (m, J 3.8, 5.8 Hz, 2H), 4.55 (s, 2H), 4.35 (d, J 5.8 Hz, 2H), 3.82 (s, 3H), 2.34 (t, J 7.4 Hz, 2H), 1.98-1.94 (m, |

| Example | Yield | Reagents | $^1$H-NMR (300 MHz, CDCl$_3$, δ) |
|---|---|---|---|
| | | | 4H), 1.60-1.55 (m, 2H), 1.23 (m, 20H), 0.84 (t, 3H). MS: M + 1 477 |
| 43<br>2-((4-hydroxy-2-iodo-5-methoxybenzyl)amino)-2-oxoethyl oleate | 50% | Intermediate 5 (example 5) and (9Z)-octadec-9-enoic acid (R$_6$—COOH) | 7.31 (s, 1H), 6.90 (s, 1H), 6.68 (br t, 1H), 5.33-5.31 (m, 2H), 4.56 (s, 2H), 4.42 (d, J 6.1 Hz, 2H), 3.83 (s, 3H), 2.38 (t, J 7.7 Hz, 2H), 2.00-1.96 (m, 4H), 1.62 (quint, J 7.1 Hz, 2H), 1.27-1.19 (m, 20H), 0.86 (t, J 6.9 Hz, 3H). MS: M − 1 600 |
| 44<br>(R,Z)-2-((4-hydroxy-3-methoxybenzyl)amino)-2-oxoethyl 12-hydroxy-octadec-9-enoate | 82% | Intermediate 3 (example 3) and (R,Z)-12-hydroxyoctadec-9-enoic acid (R$_6$—COOH) | 6.80 (d, J 8.0, 1H), 6.75 (s, 1H), 6.68 (d, J 8.0 Hz, 1H), 6.51 (br t, 1H), 5.50-5.45 (m, 1H), 5.39-5.32 (m, 1H), 4.54 (s, 2H), 4.34 (d, J 5.5 Hz, 2H), 3.80 (s, 3H), 3.57 (quint, J 5.5 Hz, 1H), 2.32 (t, J 7.4 Hz, 2H), 2.16 (t, J 6.6 Hz, 2H), 2.00-1.96 (m, 2H), 1.58- 1.54 (m, 2H), 1.41 (m, 2H), 1.23-1.16 (m, 16H), 0.83 (t, J 5.4 Hz, 3H). MS: M − 1 491 |
| 45<br>(R,Z)-2-((4-hydroxy-2-iodo-5-methoxybenzyl)-amino)-2-oxoethyl 12-hydroxyoctadec-9-enoate | 81% | Intermediate 5 (example 5) and (R,Z)-12-hydroxyoctadec-9-enoic acid (R$_6$—COOH) | 7.29 (s, 1H), 6.88 (s, 1H), 6.68 (br t, 1H), 5.49 (m, 1H), 5.37 (m, 1H), 4.56 (s, 2H), 4.41 (d, J 6.0 Hz, 2H), 3.81 (s, 3H), 3.59 (m, 1H), 2.27 (t, 7.1 Hz, 2H), 2.18 (t, J 6.3 Hz, 2H), 1.61 (m, 1H), 1.43 (s, 1H), 1.25 (m, 20H), 0.84 (t, J 6.3 Hz, 3H). MS: M − 1 617 |
| 46<br>(R,Z)-2-((4-hydroxy-3-methoxybenzyl)amino)-2-oxoethyl 12-(2-phenylacetoxy)octadec-9-enoate | 87% | Intermediate 3 (example 3) and (R,Z)-12-(2-phenylacetoyloxy) octadec-9-enoic acid (R$_6$—COOH) | 7.35-7.18 (m, 5H), 6.77 (d, J 7.9 Hz, 1H), 6.74 (d, J 1.6 Hz, 1H), 6.69-6.58 (m, 2H), 5.40 (m, 1H), 5.22 (m, 1H), 4.83 (quint, J 6.3 Hz, 1H), 4.53 (s, 2H), 4.32 (d, J 5.8 Hz, 2H), 3.78 (s, 3H), 3.54 (s, 2H), 2.32 (t, J 7.4 Hz, 2H), 2.21 (m, 2H), 1.95 (m, 2H), 1.56 (m, 2H), 1.48 (m, 2H), 1.22-1.10 (m, 16H), 0.82 (t, J 6.9 Hz, 3H). MS: M − 1 608 |
| 47<br>(R,Z)-2-((4-hydroxy-2-iodo-5-methoxybenzyl)-amino)-2-oxoethyl 12-(2-phenylacetoyloxy)-octadec-9-enoate | 92% | Intermediate 5 (example 5) and (R,Z)-12-(2-phenylacetoyloxy) octadec-9-enoic acid (R$_6$—COOH) | 7.31-7.20 (m, 6H), 6.86 (s, 1H), 6.74 (br t, 1H), 5.40 (m, 1H), 5.26 (m, 1H), 4.83 (quint, J 6.3 Hz, 1H), 4.55 (s, 2H), 4.39 (d, J 6.0 Hz, 2H), 3.79 (s, 3H), 3.55 (s, 2H), 2.36 (t, J 7.4 Hz, 2H), 2.25 (m, 2H), 1.94 (m, 2H), 1.60 (m, 2H), 1.49 (m, 2H), 1.22-1.11 (m, 16H), 0.82 (t, J 6.9 Hz, 3H). MS: M − 1 734 |
| 48<br>(Z)-2-((4-hydroxy-3-methoxybenzyl)amino)-2-oxoethyl docos-13-enoate | 85% | Intermediate 3 (example 3) and (Z)-docos-13-enoic acid (R$_6$—COOH) | 6.80 (d, J 8.0 Hz, 1H), 6.75 (d, J 1.4 Hz, 1H), 6.70 (dd, J 8.0, 1.4 Hz, 1H), 6.52 (br t, 1H), 6.05 (br s, 1H), 5.36-5.26 (m, 2H), 4.55 (s, 2H), 4.35 (d, J 5.8 Hz, 2H), 3.82 (s, 3H), 2.33 |

| Example | Yield | Reagents | $^1$H-NMR (300 MHz, CDCl$_3$, δ) |
|---|---|---|---|
| 49 (Z)-2-((4-hydroxy-2-iodo-5-methoxybenzyl)amino)-2-oxoethyl docos-13-enoate | 57% | Intermediate 5 (example 5) and (Z)-docos-13-enoic acid (R$_6$—COOH) | (t, J 7.5 Hz, 2H), 2.00-1.95 (m, 4H), 1.58 (quint, J 7.5 Hz, 2H), 1.23-1.17 (m, 28H), 0.85 (t, J 6.9 Hz, 3H). MS: M − 1 530 7.32 (s, 1H), 6.91 (s, 1H), 6.67 (br t, 1H), 5.40-5.31 (m, 2H), 4.57 (s, 2H), 4.42 (d, J 6.0 Hz, 2H), 3.86 (s, 3H), 2.38 (t, J 5.8 Hz, 2H), 2.0 (m, 4H), 1.63 (quint, J 5.8 Hz, 2H), 1.40-1.15 (m, 28H), 0.87 (t, J 6.1 Hz, 3H). MS: M − 1 656 |
| 50 (5Z,8Z,11Z,14Z)-2-((4-hydroxy-3-methoxy-benzyl)amino)-2-oxoethyl icosa-5,8,11,14-tetraenoate | 57% | Intermediate 3 (example 3) and (5Z,8Z,11Z,14Z)-icosa-5,8,11,14-tetraenoic acid (R$_6$—COOH) | 6.79 (d, J 8.0 Hz, 1H), 6.75 (d, J 1.9 Hz, 1H), 6.69 (dd, J 8.0, 1.9 Hz, 1H), 6.57 (br t, 1H), 5.38-5.27 (m, 8H), 4.54 (s, 2H), 4.33 (d, J 5.8 Hz, 2H), 3.80 (s, 3H), 2.81-2.73 (m, 6H), 2.35 (t, J 7.7 Hz, 2H), 2.10-1.98 (m, 4H), 1.67 (quint, J 7.5 Hz, 2H), 1.26 (m, 6H), 0.85 (t, J 6.9 Hz, 3H). MS: M + 1 499 |
| 51 (5Z,8Z,11Z,14Z)-2-((4-hydroxy-2-iodo-5-methoxybenzyl)amino)-2-oxoethyl icosa-5,8,11,14-tetraenoate | 82% | Intermediate 5 (example 5) and (5Z,8Z,11Z,14Z)-icosa-5,8,11,14-tetraenoic acid (R$_6$—COOH) | 7.31 (s, 1H), 6.89 (s, 1H), 6.68 (br t, 1H), 5.36-5.33 (m, 8H), 4.56 (s, 2H), 4.42 (d, J 6.0 Hz, 2H), 3.83 (s, 3H), 2.79-2.77 (m, 6H), 2.40 (t, J 7.5 Hz, 2H), 2.08 (m, 4H), 1.72 (quint, J 7.5 Hz, 2H), 1.29-1.26 (m, 6H), 0.86 (t, J 6.9 Hz, 3H). MS: M − 1 622 |
| 52 (4E,8E,12E,16E)-2-((4-hydroxy-3-methoxy-benzyl)amino)-2-oxoethyl 4,8,13,17,21-pentamethyldocosa-4,8,12,16,20-pentaenoate | 50% | Intermediate 3 (example 3) and (4E,8E,12E,16Z)-4,8,13,17,21-pentamethyl-docosa-4,8,12,16,20-pentae-noic acid (R$_6$—COOH) | 6.83 (d, J 7.9 Hz, 1H), 6.78-6.73 (m, 2H), 6.38 (br t, 1H), 5.79 (br s, 1H), 5.20-5.04 (m, 5H), 4.58 (s, 2H), 4.39 (d, J 5.8 Hz, 2H), 3.86 (s, 3H), 2.48 (t, J 7.4 Hz, 2H), 2.28 (t, J 7.4Hz, 2H), 2.10-1.90 (m, 16H), 1.65-1.50 (m, 18H). MS: M + 1 595 |
| 53 (4E,8E,12E,16E)-2-((4-hydroxy-2-iodo-5-methoxybenzyl)amino)-2-oxoethyl 4,8,13,17,21-pentamethyldocosa-4,8,12,16,20-pentaenoate | 72% | Intermediate 5 (example 5) and (4E,8E,12E,16Z)-4,8,13,17,21-pentamethyl docosa-4,8,12,16,20-pentae-noic acid (R$_6$—COOH) | 7.31 (s, 1H), 6.89 (s, 1H), 6.68 (br t, 1H), 5.94 (br s, 1H), 5.20-5.05 (m, 5H), 4.56 (s, 2H), 4.42 (d, J 6.1 Hz, 2H), 3.83 (s, 3H), 2.50 (t, J 7.3 Hz, 2H), 2.31 (t, J 7.3 Hz, 2H), 2.10-1.90 (m, 16H), 1.65-1.50 (m, 18H). MS: M − 1 719 |

Example 54

Synthesis of (E)-2-((3,4-dihydroxybenzyl)amino)-2-oxoethyl 3,7-dimethylocta-2,6-dienoate To a solution of ((4-(isocyanomethyl)-1,2-phenylene)bis(oxy))bis(tert-butyldimethylsilane) (Intermediate 8) (272 mg, 0.72 mmol) in CH$_2$Cl$_2$ (6.2 mL) 37% aqueous formaldehyde solution (215 µL, 2.88 mmol) and (E)-3,7-dimethylocta-2,6-dienoic acid (the compound R$^5$—COOH in scheme 1) (121 mg, 0.72 mmol) are added and the resulting mixture is stirred at reflux for 3 h. Then, the volatile is removed under vacuo and the product is solubilized in THF (6.5 mL) and cooled down to 0° C. At this temperature, acetic acid (140 µL, 2.45 mmol) and TBAF (2.45 mL, 2.45 mmol) are added. The reaction is stirred for 3 h. The volatile is evaporated and ethyl acetate is added, washed with water (×2), dried over sodium sulfate and evaporated to give an orange solid. The crude material is subjected to chromatography column with petroleum ether/ethyl acetate 9:1 and then petroleum ether/ethyl acetate 7:3 as eluent, given compound 54 as a white solid (47%). Analytical data: $^1$H-NMR (300 MHz, CDCl$_3$): δ 6.86-6.78 (m, 2H), 6.66 (br s, 1H), 6.63 (d, J 7.7 Hz, 1H), 5.70 (s, 1H), 5.04 (t, J 6.2 Hz, 1H), 4.63 (s, 2H), 4.36 (d, J 5.8 Hz, 2H), 2.20-2.15 (m, 7H), 1.67 (s, 3H), 1.59 (s, 3H). MS: M−1 346.

Example 55

Synthesis of (E)-2-((4,5-dihydroxy-2-iodobenzyl) amino)-2-oxoethyl 3,7-dimethylocta-2,6-dienoate To a solution of ((4-iodo-5-(isocyanomethyl)-1,2-phenylene)bis(oxy))bis(tert-butyldimethyl-silane) (Intermediate 9) (252 mg, 0.50 mmol) in $CH_2Cl_2$ (4.5 mL) 37% aqueous formaldehyde solution (150 µL, 2 mmol) and (E)-3,7-dimethylocta-2,6-dienoic acid (the compound $R^5$—COOH in scheme 1) (84 mg, 0.50 mmol) are added and the resulting mixture is stirred at reflux for 3.30 h. Then, the volatile is removed under reduced pressure and the product is solubilized in THF (4.5 mL) and cooled down to 0° C. At this temperature, acetic acid (97 µL, 1.70 mmol) and TBAF (1.70 mL, 1.70 mmol) are added. The reaction is stirred for 2 h. The volatile is evaporated and ethyl acetate is added, washed with water (×2), dried over sodium sulfate and evaporated to give an orange solid. The crude material is subjected to chromatography column with petroleum ether/ethyl acetate 8:2 and then petroleum ether/ethyl acetate 7:3 as eluent, given compound 55 as a sticky orange solid (91 mg, 192 mmol, 39%). Analytical data: $^1$H-NMR (300 MHz; $CDCl_3$): δ 7.26 (s, 1H), 7.08 (br t, J 6.0 Hz, 1H), 6.98 (s, 1H), 5.73 (s, 1H), 5.05 (t, J 5.4 Hz, 1H), 4.62 (s, 2H), 4.40 (d, J 6.0 Hz, 2H), 2.17-2.15 (m, 7H), 1.70 (s, 3H), 1.60 (s, 3H) MS: M−1 472

Following the same synthetic route for example 54 and using the same reagents and intermediates unless otherwise indicated in the table below, the following compounds were obtained:

| Example | Yield | Reagents | $^1$H-NMR (300 MHz, $CDCl_3$, δ) |
|---|---|---|---|
| 56 (4E,8E,12E,16E)-2-((3,4-dihydroxybenzyl)-amino)-2-oxoethyl 4,8,13,17,21-pentamethyldocosa-4,8,12,16,20-pentaenoate | 56% | Intermediate 8 (example 8) and (4E,8E,12E, 16E)-4,8,13,17, 21-pentamethyl-docosa-4,8,12,16,20-pentaenoic acid ($R_6$—COOH) | 6.81-6.79 (m, 2H), 6.64 (d, J 7.7 Hz, 1H), 6.55 (br s, 1H), 5.12-5.10 (m, 5H), 4.60 (s, 2H), 4.35 (d, J 4.9 Hz, 2H), 2.45 (t, J 7.4 Hz, 2H), 2.28 (t, J 7.4 Hz, 2H), 2.04-1.99 (m, 16H), 1.67-1.60 (m, 18H). MS: M − 1 579 |
| 57 (4E,8E,12E,16E)-2-((4,5-dihydroxy-2-iodobenzyl)amino)-2-oxoethyl 4,8,13,17,21-pentamethyldocosa-4,8,12,16,20-pentaenoate | 63% | Intermediate 9 (example 9) and (4E,8E,12E, 16E)-4,8,13,17, 21-pentamethyl-docosa-4,8,12,16,20-pentae noic acid ($R_6$—COOH) | 7.29 (s, 1H), 7.04 (s, 1H), 7.00 (br s, 1H), 5.81 (br s, 1H), 5.11-5.09 (m, 5H), 4.60 (s, 2H), 4.43 (d, J 6.1 Hz, 2H), 2.52 (t, J 7.1 Hz, 2H), 2.32 (t, J 7.1 Hz, 2H), 2.06-1.99 (m, 16H), 1.67 (s, 3H), 1.60-1.58 (m, 15H). MS: M − 1 705 |

Example 58

Synthesis of (E)-2-((3,4-dihydroxyphenethyl)amino)-2-oxoethyl 3,7-dimethylocta-2,6-dienoate To a solution of ((4-(2-isocyanoethyl)-1,2-phenylene)bis(oxy))bis(tert-butyldimethylsilane) (Intermediate 13) (283 mg, 0.72 mmol) in $CH_2Cl_2$ (6.2 mL) 37% aqueous formaldehyde solution (215 μL, 2.88 mmol) and (E)-3,7-dimethylocta-2,6-dienoic acid (the compound $R^5$—COOH in scheme 1) (121 mg, 0.72 mmol) are added and the resulting mixture is stirred at reflux for 3 h. Then, the volatile is removed under reduced pressure and the product is solubilized in THF (6.5 mL) and cooled down to 0° C. At this temperature, acetic acid (140 μL, 2.45 mmol) and TBAF (2.45 mL, 2.45 mmol) are added. The reaction is stirred for 2 h. The volatile is evaporated and ethyl acetate is added, washed with water (×2), dried over sodium sulfate and evaporated to give an orange solid. The crude product is subjected to chromatography column with petroleum ether/ethyl acetate 7:3 and then petroleum ether/ethyl acetate 5:5 as eluent, yielding compound 58 as a colorless oil (138 mg, 0.38 mmol, 53%). Analytical data: 1H-NMR (300 MHz; CDCl3): δ 6.75 (d, J 7.6 Hz, 1H), 6.69 (s, 1H), 6.56 (br s, 1H), 6.49 (d, J 7.6 Hz, 1H), 5.66 (s, 1H), 5.04 (t, J 6.2 Hz, 1H), 4.54 (s, 2H), 3.44 (t, J 6.5 Hz, 2H), 2.63 (t, J 6.5 Hz, 2H), 2.15-2.03 (m, 7H), 1.66 (s, 3H), 1.58 (s, 3H). MS: M−1 360.

Following the same synthetic route for example 58 and using the same reagents and intermediates unless otherwise indicated in the table below, the following compounds were obtained:

| Example | Yield | Reagents | $^1$H-NMR (300 MHz, CDCl$_3$, δ) |
|---|---|---|---|
| 59<br>(E)-2-((4,5-dihydroxy-2-iodophenethyl)amino)-2-oxoethyl 3,7-dimethyl-octa-2,6-ienoate | 44% | Intermediate 15 (example 15) and (E)-3,7-dimethylocta 2,6-dienoic acid (R$_6$—COOH) | 7.69 (br s, 1H), 7.29 (s, 1H), 6.75 (s, 1H), 6.32 (br s, 1H), 5.86 (br s, 1H), 5.73 (s, 1H), 5.07 (t, J 6.2 Hz, 1H), 4.59 (s, 2H), 3.51 (q, J 6.8 Hz, 2H), 2.86 (t, J 6.8 Hz, 2H), 2.19-2.16 (m, 7H), 1.69 (s, 3H), 1.61 (s, 3H). MS: M − 1 486 |
| 60<br>(4E,8E,12E,16E)-2-((3,4-dihydroxy-phenethyl)amino)-2-oxoethyl 4,8,13,17,21-pentamethyldocosa-4,8,12,16,20-pentaenoate | 18% | Intermediate 13 (example 13) and (4E,8E,12E,16E)-4,8,13,17, 21-pentamethyl-docosa-4,8,12,16,20-pentae-noic acid | 6.79-6.69 (m, 2H), 6.53 (d, J 6.9 Hz, 1H), 6.34 (br s, 1H), 5.13-5.11 (m, 5H), 4.52 (s, 2H), 3.47 (q, J 6.9 Hz, 2H), 2.67 (t, J 6.9 Hz, 2H), 2.45 (t, J 7.1 Hz, 2H) 2.26 (t, J 7.1 Hz, 2H), 2.04-1.99 (m, 16H), 1.67-1.59 (m, 18H). MS: M − 1 593 |
| 61<br>(4E,8E,12E,16E)-2-((4,5-dihydroxy-2-iodophenethyl)amino)-2-oxoethyl 4,8,13,17,21-pentamethyldocosa-4,8,12,16,20-pentaenoate | 33% | Intermediate 15 (example 15) and (4E,8E,12E,16E)-4,8,13,17,21-pentamethyl-docosa-4,8,12,16,20-pentae-noic acid | 7.28 (s, 1H), 6.76 (s, 1H), 6.51 (br s, 1H), 5.13-5.09 (m, 5H), 4.56 (s, 2H), 3.48 (q, J 6.3 Hz, 2H), 2.82 (t, J 6.3 Hz, 2H), 2.49 (t, J 7.4 Hz, 2H), 2.28 (t, J 7.4 Hz, 2H), 2.04-1.99 (m, 16H), 1.67-1.46 (m, 18H). MS: M − 1 719 |
| 62<br>2-((3,4-dihydroxy-phenethyl)amino)-2-oxoethyl oleate | 67% | Intermediate 13 (example 13) and oleic acid | 7.03 (br s, 1H), 6.81 (d, J 7.7 Hz, 1H), 6.69 (d, J 1.8, 1H) 6.57 (dd, J 7.7 Hz, 1H), 6.25 (br s, 1H), 6.10 (br s, 1H), 5.35-5.32 (m, 2H), 4.54 (s, 2H), 3.52 (q, J 6.9 Hz, 2H), 2.70 (t, J 6.9 Hz, 2H), 2.33 (t, J 7.4 Hz, 2H), 2.04-1.99 (m, 4H), 1.59 (quint, J 7.4 Hz, 2H), 1.29-1.21 (m, 20H), 0.87 (t, J 6.6 Hz, 3H). MS: M − 1 475 |
| 63<br>2-((4,5-dihydroxy-2-iodophenethyl)amino)-2-oxoethyl oleate | 61% | Intermediate 15 (example 15) and oleic acid | 7.30 (s, 1H), 6.75 (s, 1H), 6.36 (br s, 1H), 5.34 (m, 2H), 4.56 (s, 2H), 3.52 (q, J 6.8 Hz, 2H), 2.85 (t, J 6.8 Hz, 2H), 2.38 (t, J 7.4 Hz, 2H), 2.01-1.99 (m, 4H), 1.61 (quint, J 7.4 Hz, 2H), 1.29-1.26 (m, 20H), 0.87 (t, J 7.1 Hz, 3H). MS: M − 1 601 |
| 64<br>(5Z,8Z,11Z,14Z)-2-((3,4- | 65% | Intermediate 13 (example 13) and | 6.80 (d, J 6.9 Hz, 1H), 6.69 (d, J 1.6, 1H), |

-continued

| Example | Yield | Reagents | $^1$H-NMR (300 MHz, CDCl$_3$, δ) |
|---------|-------|----------|-----------------------------------|
| dihydroxyphenethyl)amino)-2-oxoethyl icosa-5,8,11,14-tetraenoate | | (5Z,8Z,11Z,14Z)-methyl icosa-5,8,11,14-tetraenoic acid | 6.56 (dd, J 6.9 Hz, 1H), 6.26 (br s, 1H), 5.39-5.35 (m, 8H), 4.54 (s, 2H), 3.50 (q, J 6.8 Hz, 2H), 2.84-2.81 (m, 6H), 2.70 (t, J 6.8 Hz, 2H), 2.35 (t, J 7.4 Hz, 2H), 2.14-2.01 (m, 4H), 1.67 (quint, J 7.4 Hz, 2H), 1.37-1.28 (m, 6H), 0.88 (t, J 6.9 Hz, 3H). MS: M − 1 497 |
| 65 (5Z,8Z,11Z,14Z)-2-((4,5-dihydroxy-2-iodo-phenethyl)amino)-2-oxoethyl icosa-5,8,11,14-tetraenoate | 76% | Intermediate 15 (example 15) and (5Z,8Z,11Z,14Z)-methyl icosa-5,8,11,14-tetraenoic acid | 7.30 (s, 1H), 6.74 (s, 1H), 6.34 (br s, 1H), 5.40-5.36 (m, 8H), 4.56 (s, 2H), 3.51 (q, J 6.3 Hz, 2H), 2.85-2.80 (m, 8H), 2.40 (t, J 7.4 Hz, 2H), 2.15-2.01 (m, 4H), 1.70 (quint, J 7.4 Hz, 2H), 1.37-1.29 (m, 6H), 0.88 (t, J 6.7 Hz, 3H). MS: M − 1 623 |

Determination of the Compound Activity on TRPV1

The activity of the compounds was determined on TRPV1 expressing cells (TRPV1-SH-SY5Y) by Calcium microfluorometry assay. The efficacy of the more potent compounds was also determined.

(A) In Vitro Activity Assays

SH-SY5Y cells stably expressing rat TRPV1 channel (SH-SY5Y-TRPV1) were grown in Earle's minimum essential medium (MEM) containing 10% (v/v) of FCS, 1% nonessential amino acids, 2 mM L-glutamine, 100 μg/ml streptomycin, 100 U/ml penicillin, and 0.4 μg/ml puromycin in a humidity-controlled incubator with 5% CO$_2$ and at 37° C. For fluorescence assays, cells expressing TRPV1 channel (TRPV1-SH-SY5Y) were seeded in 96-well plates (Corning Incorporated, Corning, N.Y.) at a cell density of 40,000 cells 2 days before treatment. The day of treatment the medium was replaced with 100 μL of the dye loading solution Fluo-4 NW supplemented with probenecid 2.5 mM. After incubation at 37° C. in a humidified atmosphere of 5% CO$_2$ for 60 minutes, plates were transferred to a fluorescence plate reader (Polastar Omega BMG Labtech). The baseline fluorescence of Fluo-4 dye (emission 485 nm/excitation 520 nm) was recorded for 4 cycles. Then, 1 μL of vehicle (DMSO) or compounds at 10 μM final concentration were added to the well, and fluorescence intensity was recorded during 10 cycles more prior to stimulation with the agonist (10 μM capsaicin for TRPV1). The antagonist (10 μM Ruthenium Red for TRPV1) was added for the blockade. The changes in fluorescence intensity were recorded during 10 cycles more. The results are shown in table 2 below.

TABLE 2

| Compounds | TRPV1 activation at 10 μM (% ± SD) | TRPV1 blockage at 10 μM (% ± SD) |
|-----------|-----------------------------------|----------------------------------|
| Cap | 100% | |
| RR | | 100% |
| Ex-16 | 25.59 ± 4.29 | |
| Ex-17 | | 14.44 ± 0.27 |
| Ex-18 | 29.43 ± 14.90 | |
| Ex-19 | | 21.85 ± 2.85 |
| Ex-20 | 35.82 ± 3.48 | |
| Ex-21 | | 8.35 ± 4.10 |

TABLE 2-continued

| Compounds | TRPV1 activation at 10 μM (% ± SD) | TRPV1 blockage at 10 μM (% ± SD) |
|-----------|-----------------------------------|----------------------------------|
| Ex-22 | 73.32 ± 12.83 | |
| Ex-23 | | 23.14 ± 7.81 |
| Ex-24 | 75.59 ± 6.25 | |
| Ex-25 | | 13.98 ± 5.98 |
| Ex-26 | 74.41 ± 17.66 | |
| Ex-27 | | 21.80 ± 5.41 |
| Ex-28 | 54.08 ± 4.09 | |
| Ex-29 | | 31.23 ± 8.34 |
| Ex-30 | 68.45 ± 7.20 | |
| Ex-31 | | 25.23 ± 7.63 |
| Ex-32 | 75.90 ± 2.49 | |
| Ex-33 | | 77.28 ± 11.85 |
| Ex-34 | 47.91 ± 10.32 | |
| Ex-35 | | 20.48 ± 9.67 |
| Ex-36 | 74.80 ± 8.30 | |
| Ex-37 | | 43.18 ± 10.07 |
| Ex-38 | 75.96 ± 9.86 | |
| Ex-39 | | 21.82 ± 4.75 |
| Ex-40 | 54.74 ± 17.75 | |
| Ex-41 | | 38.89 ± 3.53 |
| Ex-42 | 77.19 ± 11.95 | |
| Ex-43 | | 45.68 ± 14.26 |
| Ex-44 | 60.84 ± 12.80 | |
| Ex-45 | | 21.74 ± 7.05 |
| Ex-46 | 33.16 ± 9.97 | |
| Ex-47 | | 63.29 ± 12.80 |
| Ex-48 | 47.40 ± 14.56 | |
| Ex-49 | | 34.94 ± 5.51 |
| Ex-50 | 73.80 ± 7.42 | |
| Ex-51 | | 30.85 ± 5.87 |
| Ex-52 | 79.31 ± 6.41 | |
| Ex-53 | | 31.05 ± 1.46 |
| Ex-54 | 77.42 ± 5.17 | |
| Ex-55 | | 104.22 ± 12.65 |
| Ex-56 | 83.71 ± 6.00 | |
| Ex-57 | | 12.23 ± .9.31 |
| Ex-58 | 88.12 ± 9.76 | |
| Ex-59 | | 46.3 ± 12.70 |
| Ex-60 | 75.76 ± 6.64 | |
| Ex-61 | | 8.26 ± 1.53 |
| Ex-62 | 78.48 ± 4.61 | |
| Ex-63 | | 1.13 ± 5.56 |
| Ex-64 | 79.05 ± 11.25 | |
| Ex-65 | | 6.71 ± 2.18 |

(B) Dose Response Measurements

The most potent compounds were selected to calculate $EC_{50}$ and $IC_{50}$. Normalized responses (%) versus log [μM] were adjusted to a non-linear fit with variable slope, a four-parameter dose-response curve $Y=100/(1+10^{\wedge}((LogEC50-X)*HillSlope))$ where X=% normalized response and Y=log [μM] or just dose-response curve $Y=100/(1+10^{\wedge}((LogEC50-X)))$. $EC_{50}$ are expressed with 95% confident interval followed by $r^2$ for regression adjustment. All data are expressed as mean±standard error of the mean (SD). Each condition was assessed by triplicate (n=3) in 3 independent experiments (N=3). Table 3 shows the results.

TABLE 3

| Compound | $EC_{50}$ (μM) ± SD | $IC_{50}$ (μM) ± SD |
|---|---|---|
| Capsaicin | 2.32 ± 22 | |
| Ex-32 | 0.28 ± 0.08 | |
| Ex-33 | | 0.32 ± 0.25 |
| Ex-36 | 0.08 ± 0.03 | |
| Ex-37 | | 0.86 ± 0.51 |
| Ex-52 | 0.04 ± 0.008 | |
| Ex-54 | 0.11 ± 0.02 | |
| Ex-55 | | 6.82 ± 1.38 |
| Ex-56 | 0.015 ± 0.02 | |

(A) In Vivo Activity Assays

Model of Inflammatory Pain

One of the compounds with higher potency (Ex-37) was selected to be tested in a model of inflammatory pain. C57-mice (≈30 g) were used for the study. C57BL/6 were obtained from Janvier, France. Complete Freund's adjuvant (CFA) emulsion (1:1 oil/saline, 0.5 mg/ml) was injected into the plantar surface (10 μl) of the right hind paw (Garcia-Martinez et al., 2006). 24 h after CFA injection, compound Ex-37 was administered intravenously (at 1 mg/kg, 3 mg/kg or 10 mg/kg) or intraplantar (at 10 mg/kg, 30 mg/kg or 100 mg/kg)) on the right hind paw. Thermal hyperalgesia was monitored 24 h after CFA injection and up to 2 h after administering the compound with an Ugo Basile Dynamic Plantar Aesthesiometer as reported previously (Garcia-Martinez et al., 2006). In brief, mice were habituated to an apparatus consisting of individual Perspex boxes on an elevated glass table. A mobile radiant heat source was located under the table and focused on the hind paw. Paw withdrawal latencies were defined as the time taken by the mouse to remove its hind paw from the heat source. A cutoff point of 25 s was set to prevent tissue damage. The compound Ex-37 showed antinociceptive effects in the thermal hyperalgesia test both when administered intravenously (FIG. 1) and intraplantar (FIG. 2).

Figure 2:
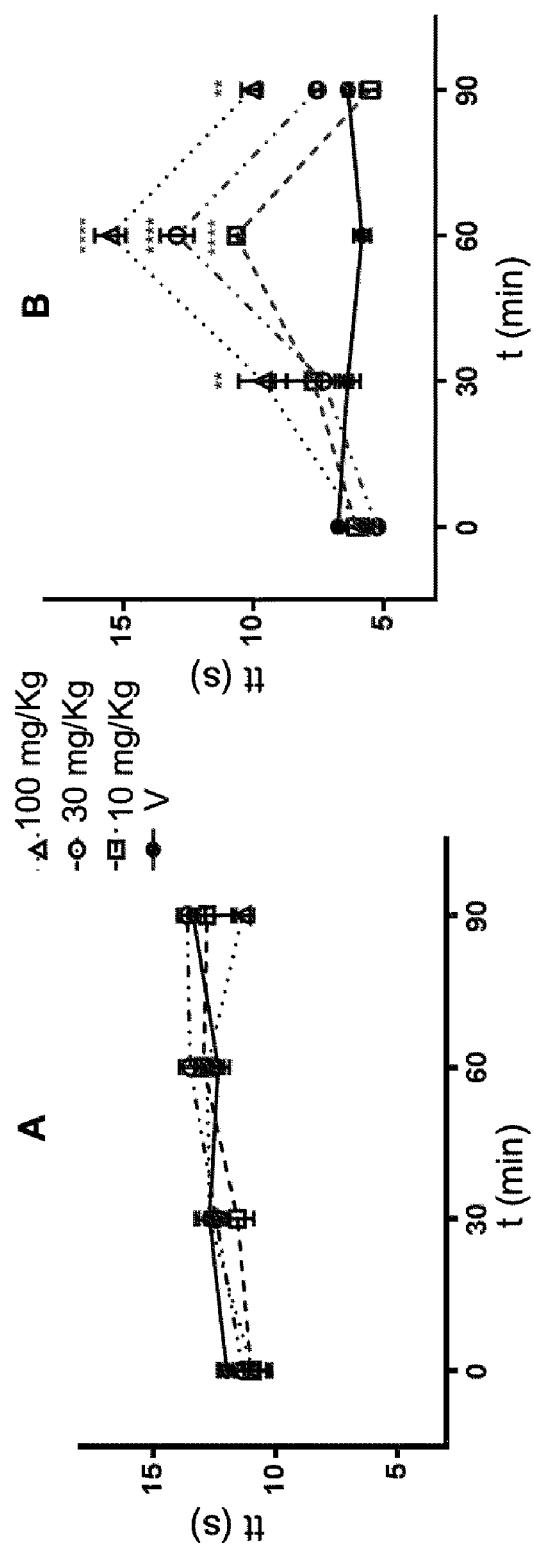
FIG. 2 shows the effect of a compound of the invention (Ex-37) by intraplantar administration in the CFA-induced paw inflammation model in comparison to vehicle (V) in the left (A) and in the right hind paw (B). The diagram shows the paw withdrawal latencies (tt) over time (t) in response to thermal stimulation (n=6 mice/group). Data are given as mean±SEM n=6. 2-way ANOVA with Bonferroni post hoc test. *$P<0.05$; $P<0.01$, *$P<0.001$, ***$P<0.0001$.

As can be seen both in in FIG. 1 (B) and FIG. 2 (B), the effect of the compound of the invention was significant in the right hind paw where the compound had been administered. The antinociceptive effect increased over time until reaching the highest level at 60 min. Importantly, the effect decreased after this time point. On the other hand, no significant effect was observed in the left hind paw FIG. 1 (A) and FIG. 2 (A), were no compound had been administered (control). Besides, lack of toxicity of the compound was evidenced when it the compound was intravenously injected at high doses such as 10 mg/kg.

Histamine-induced Licking Behavior

Figure 3:
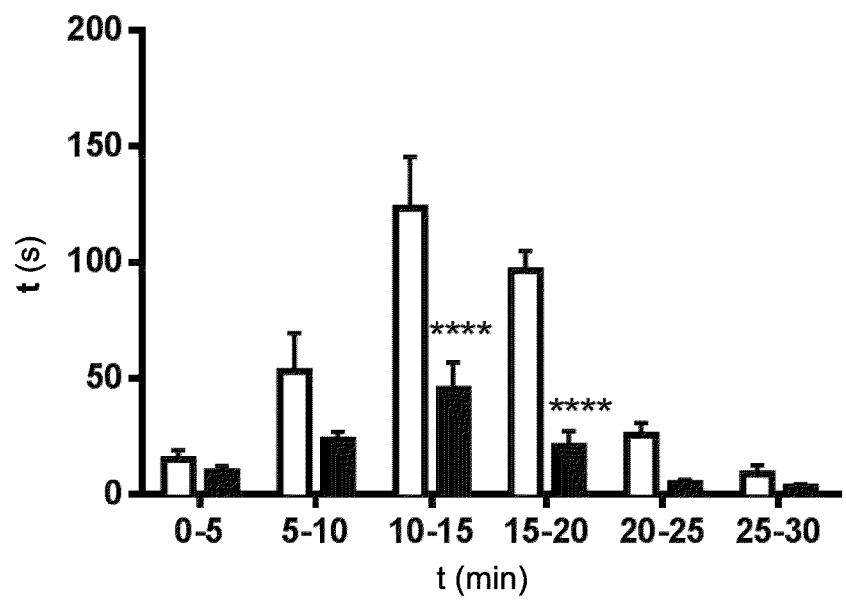
FIG. 3 shows the effect of a compound of the invention (Ex-37) (black bars) in comparison to control (white bars) in an in vivo model of itch consisting in the measurement of the histamine-induced licking behavior. The diagram shows the time spent in licking the injected paw with respect to time after histamine injection (t (min)). ****$p<0.001$.

Ex-37 was tested in a model of itch (FIG. 3). C57-mice (≈30 g) were placed into transparent plastic cages, and after a 10 min habituation period they were intraplantarlly injected with 125 μg of histamine in 25 μL of saline. Immediately after the injection of histamine, the animals were returned to the observation cages and the time spent in licking the injected paw during a 30 min period was recorded and measured manually with a chronometer (FIG. 3, white bars). Animals receiving Ex-37 (100 μg) were administered by injection with the compound 30 min before histamine injection (FIG. 3, black bars, ****p<0.001).

The antipruritogenic effect of the compound of the invention was evident during all the time measured reaching the highest and significant effect between 10 and 20 min after histamine injection.

Chloroquine-induced Pruritus

Figure 4:
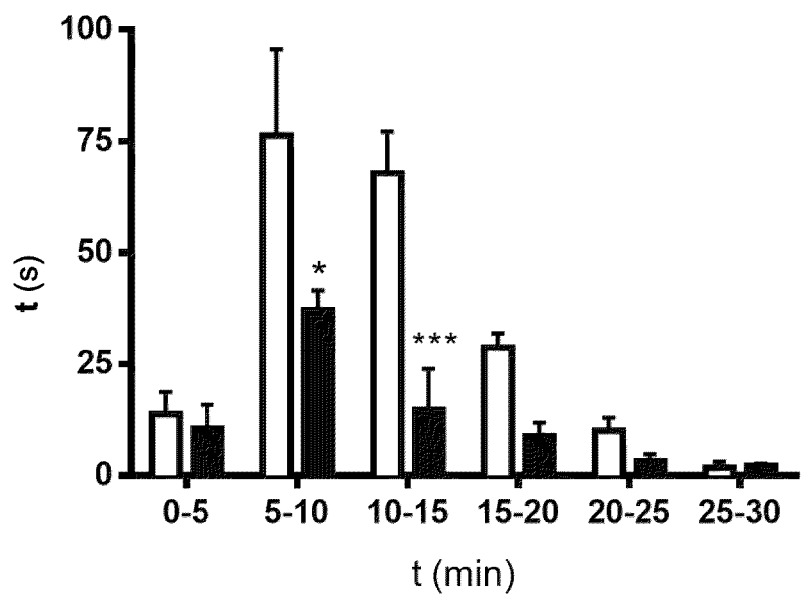
FIG. 4 shows the effect of a compound of the invention (Ex-37) (black bars) in comparison to control (white bars) in an in vivo model of non-histaminergic pruritus consisting in the measurement of the chloroquine-induced pruritus licking behavior. The diagram shows the time spent in licking the injected paw with respect to time after chloroquine injection (t (min)). *$p<0.05$, ****$p<0.001$.

Ex-37 was evaluated in a model of non-histaminergic pruritus (FIG. 4). C57-mice (≈30 g) were placed into transparent plastic cages, and after 10 min habituation, they were intraplantarly injected with 200 μg of chloroquine in 25 μL of saline. Immediately after chloroquine injection, animals were returned to observation cages. Time spent in licking the injected paw during a 30 min period was recorded and measured with a chronometer (FIG. 4, white bars). Ex-37 was intraplantarly administered at 100 μg/paw 30 min before chloroquine injection (FIG. 4, black bars, *p<0.05, ***p<0.001).

The anti-pruritogenic effect of the compound of the invention was evident during all the time measured. The highest and significant anti-itching effect was noticed between 5 and 15 min after chloroquine injection, corresponding to the highest chloroquine-induced licking behavior.

CITATION LIST

Bode, A. M. et al. "The two faces of capsaicin" Cancer Res. 2011, 71(8), 2809-2814

Li S. et al, "TRPV1 antagonist AMG9810 promotes mouse skin tumorigenesis through EGFR/Akt signalling", Carcinogenesis 2011, 32 (5), pp. 779-785.

Collado et al, "Metalation vs Nucleophilic Addition in the Reactions of N-Phenethylimides with Organolithium Reagents. Ready Access to Isoquinoline Derivatives via N-Acyliminium Ions and Parham-Type Cyclizations", J. Org. Chem. 1997, 62, 2080-2092.

Collado et al., "Parham-type Cyclization and Nucleophilic Addition-N-Acyliminium ion Cyclization Sequences for the Construction of the Isoquinoline Nucleus", Tetrahedron Letters 1996, Vol. 37, No. 34, pp. 6193-6196.

Green and P. G. M. Wuts, Protective Groups in Organic Chemistry, Wiley, 3rd ed. 1999, Chapter 2, pp. 17-200.

Weber L V et al., "Expression and functionality of TRPV1 in breast cancer cells", Breast Cancer. 2016 13, 8, pp. 243-252.

Moran M M et al., "Transient receptor potential channels as therapeutic targets", Nat. Rev. Drug Discov. 2011, 10(8), pp. 601-20.

García-Martinez C et al., "Design and characterization of a noncompetitive antagonist of the transient receptor potential vanilloid subunit 1 channel with in vivo analgesic and anti-inflammatory activity", J. Pain 2006, 7(10), pp. 735-46.

In Kueper T. et al., "Inhibition of TRPV1 for the treatment of sensitive skin", Exp. Dermatol. 2010, 19(11), pp. 980-6.

Lee, Y. M, et al, "The role of TRPV1 channel in aged human skin", Journal of Dermatological Science 2012, 65, pp. 81-85.

Tóth B. I., et al., "TRP channels in the skin", Br. J. Pharmacol. 2014, 171(10), pp. 2568-2581.

Schaible H G, "Nociceptive neurons detect cytokines in arthritis", Arthritis Res Ther. 2014, 16(5), 470.

Tóth B I et al, "Transient receptor potential vanilloid-1 signaling as a regulator of human sebocyte biology" J Invest Dermatol. 2009, 129(2), pp. 329-39.

Yun J W et al., "Antipruritic effects of TRPV1 antagonist in murine atopic dermatitis and itching models", J Invest Dermatol. 2011, 131(7), pp. 1576-9.

The invention claimed is:

1. A compound of formula (I), or a pharmaceutically, veterinary or cosmetically acceptable salt thereof, or any stereoisomer or mixtures thereof, either of the compound of formula (I) or of any of its pharmaceutically, veterinary or cosmetically acceptable salts

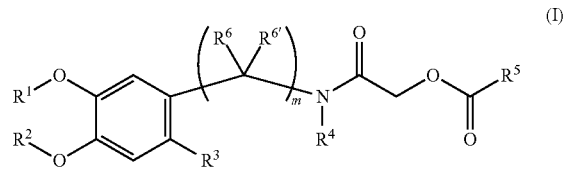

(I)

wherein
m is an integer selected from 1 to 3;
$R^1$, $R^6$ and $R^{6'}$ are independently selected from the group consisting of H, $(C_1-C_8)$alkyl, and unsaturated $(C_2-C_8)$ hydrocarbon;
  wherein $(C_1-C_8)$alkyl, unsaturated $(C_2-C_8)$hydrocarbon, and $(C_3-C_6)$cycloalkyl are optionally substituted with one or more substituents selected from the group consisting of halogen, —COOH, —OH, —NH$_2$, —COOR$^6$, —NO$_2$, —CF$_3$, —OCF$_3$, —CN, —OR$^6$, —CONH$_2$, —CONHR$^6$, —NHR$^6$, —NHCOR$^6$, —NHSO$_2$R$^6$, and —SO$_2$NHR$^6$;
$R^2$ is H;
$R^3$ is hydrogen or halogen;
$R^4$ is selected from the group consisting of H, $(C_1-C_8)$ alkyl, unsaturated $(C_2-C_8)$hydro-carbon; wherein $(C_1-C_8)$alkyl and unsaturated $(C_2-C_8)$hydrocarbon are optionally substituted with one or more substituents selected from the group consisting of halogen, —COOH, —OH, —NH$_2$, —COOR$^6$, —NO$_2$, —CF$_3$, —OCF$_3$, —CN, —OR$^6$, —CONH$_2$, —CONHR$^6$, —NHR$^6$, —NHCOR$^6$, —NHSO$_2$R$^6$, and —SO$_2$NHR$_6$;
$R^5$ is selected from the group consisting of $(C_3-C_{28})$alkyl, unsaturated $(C_3-C_{28})$hydrocarbon, and

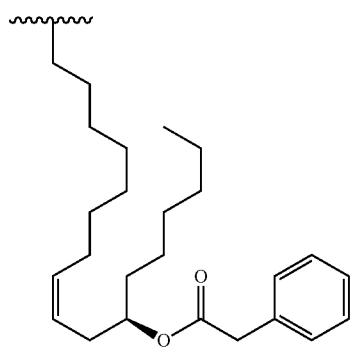 [SMILES: *CCCCCCC/C=C\C[C@@H](CCCCCC)OC(=O)Cc1ccccc1]

wherein $(C_3-C_{28})$alkyl and unsaturated $(C_3-C_{28})$hydrocarbon are optionally substituted with one or more substituents selected from the group consisting of halogen, —COOH, —OH, —NH$_2$, —COOR$^6$, —NO$_2$, —CF$_3$, —OCF$_3$, —CN, —OR$^6$, —CONH$_2$, —CONHR$^6$, —NHR$^6$, —NHCOR$^6$, —NHSO$_2$R$^6$, and —SO$_2$NHR$^6$.

2. The compound of formula (I) according to claim 1, wherein m is an integer selected from 1 to 2.

3. The compound of formula (I) according to claim 1, wherein $R^1$ is selected from the group consisting of H and optionally substituted $(C_1-C_8)$alkyl.

4. The compound of formula (I) according to claim 3, wherein $R^4$ is selected from the group consisting of H and optionally substituted $(C_1-C_8)$alkyl.

5. The compound of formula (I) according to claim 3, wherein $R^6$ and $R^{6'}$ are independently selected from the group consisting of H and optionally substituted $(C_1-C_8)$ alkyl.

6. The compound of formula (I) according to claim 1, wherein $R^3$ is H.

7. The compound of formula (I) according to claim 1, wherein $R^3$ is halogen.

8. The compound of formula (I) according to claim 1, wherein $R^4$ is selected from the group consisting of H and optionally substituted $(C_1-C_8)$alkyl.

9. The compound of formula (I) according to claim 8, wherein $R^6$ and $R^{6'}$ are independently selected from the group consisting of H and optionally substituted $(C_1-C_5)$ alkyl.

10. The compound of formula (I) according to claim 1, wherein $R^6$ and $R^{6'}$ are independently selected from the group consisting of H and optionally substituted $(C_1-C_8)$ alkyl.

11. The compound of formula (I) according to claim 1, which is selected from the group consisting of:
  2-((4-hydroxy-3-methoxy-benzyl)amino)-2-oxoethyl butyrate;
  2-((4-hydroxy-2-iodo-5-methoxybenzyl)amino)-2-oxoethyl butyrate;
  2-((4-hydroxy-3-methoxy-benzyl)amino)-2-oxoethyl pentanoate;
  2-((4-hydroxy-2-iodo-5-methoxybenzyl)amino)-2-oxoethyl pentanoate;
  2-((4-hydroxy-3-methoxy-benzyl)amino)-2-oxoethyl 3-methylbutanoate;
  2-((4-hydroxy-2-iodo-5-methoxybenzyl)amino)-2-oxoethyl 3-methyl-butanoate;
  2-((4-hydroxy-3-methoxy-benzyl)amino)-2-oxoethyl hexanoate;
  2-((4-hydroxy-2-iodo-5-methoxybenzyl)amino)-2-oxoethyl hexanoate;
  (2E,4E)-2-((4-hydroxy-3-methoxybenzyl)amino)-2-oxoethyl hexa-2,4-dienoate;
  (2E,4E)-2-((4-hydroxy-2-iodo-5-methoxybenzyl)amino)-2-oxoethyl hexa-2,4-dienoate;
  2-((4-hydroxy-3-methoxy-benzyl)amino)-2-oxoethyl heptanoate;
  2-((4-hydroxy-2-iodo-5-methoxybenzyl)amino)-2-oxoethyl heptanoate;
  2-((4-hydroxy-3-methoxy-benzyl)amino)-2-oxoethyl octanoate;
  2-((4-hydroxy-2-iodo-5-methoxybenzyl)amino)-2-oxoethyl octanoate;
  2-((4-hydroxy-3-methoxybenzyl)amino)-2-oxoethyl nonanoate;
  2-((4-hydroxy-2-iodo-5-methoxybenzyl)amino)-2-oxoethyl nonanoate;
  (E)-2-((4-hydroxy-3-methoxy-benzyl)amino)-2-oxoethyl 3,7-dimethylocta-2,6-dienoate;

(E)-2-((4-hydroxy-2-iodo-5-methoxybenzyl)amino)-2-oxoethyl 3,7-dimethylocta-2,6-dienoate;
2-((4-hydroxy-3-methoxy-benzyl)amino)-2-oxoethyl decanoate;
2-((4-hydroxy-2-iodo-5-methoxybenzyl)amino)-2-oxoethyl decanoate;
2-((4-hydroxy-3-methoxy-benzyl)amino)-2-oxoethyl dodecanoate;
2-((4-hydroxy-2-iodo-5-methoxybenzyl)amino)-2-oxoethyl dodecanoate;
2-((4-hydroxy-3-methoxy-benzyl)amino)-2-oxoethyl pentadecanoate;
2-((4-hydroxy-2-iodo-5-methoxybenzyl)amino)-2-oxoethyl pentadecanoate;
2-((4-hydroxy-3-methoxy-benzyl)amino)-2-oxoethyl stearate;
2-((4-hydroxy-2-iodo-5-methoxybenzyl)amino)-2-oxoethyl stearate;
2-((4-hydroxy-3-methoxy-benzyl)amino)-2-oxoethyl oleate;
2-((4-hydroxy-2-iodo-5-methoxybenzyl)amino)-2-oxoethyl oleate;
(R,Z)-2-((4-hydroxy-3-methoxybenzyl)amino)-2-oxoethyl 12-hydroxyoctadec-9-enoate;
(R,Z)-2-((4-hydroxy-2-iodo-5-methoxybenzyl)amino)-2-oxoethyl 12-hydroxyoctadec-9-enoate;
(Z)-2-((4-hydroxy-3-methoxy-benzyl)amino)-2-oxoethyl 12-(2-phenylacetoxy)octadec-9-enoate;
(Z)-2-((4-hydroxy-2-iodo-5-methoxybenzyl)amino)-2-oxoethyl 12-(2-phenyl-acetoxy)octadec-9-enoate;
(Z)-2-((4-hydroxy-3-methoxybenzyl)amino)-2-oxoethyl docos-13-enoate;
(Z)-2-((4-hydroxy-2-iodo-5-methoxybenzyl)amino)-2-oxoethyl docos-13-enoate;
(5Z,8Z,11Z,14Z)-2-((4-hydroxy-3-methoxy-benzyl)amino)-2-oxoethyl icosa-5,8,11,14-tetraenoate;
(5Z,8Z,11Z,14Z)-2-((4-hydroxy-2-iodo-5-methoxy-benzyl)amino)-2-oxoethyl icosa-5,8,11,14-tetraenoate;
(4E,8E,12E,16E)-2-((4-hydroxy-3-methoxybenzyl)-amino)-2-oxoethyl 4,8,13,17,21-pentamethyldocosa-4,8,12,16,20-pentaenoate;
(4E,8E,12E,16E)-2-((4-hydroxy-2-iodo-5-methoxy-benzyl)amino)-2-oxoethyl 4,8,13,17,21-pentamethyl-docosa-4,8,12,16,20-pentaenoate;
(E)-2-((3,4-dihydroxybenzyl)-amino)-2-oxoethyl 3,7-dimethylocta-2,6-dienoate;
(E)-2-((4,5-dihydroxy-2-iodo-benzyl)amino)-2-oxoethyl 3,7-dimethylocta-2,6-dienoate;
(4E,8E,12E,16E)-2-((3,4-dihydroxybenzyl)amino)-2-oxoethyl 4,8,13,17,21-pentamethyldocosa-4,8,12,16,20-pentaenoate;
(4E,8E,12E,16E)-2-((4,5-dihydroxy-2-iodobenzyl)-amino)-2-oxoethyl 4,8,13,17,21-pentamethyl-docosa-4,8,12,16,20-pentaenoate;
(E)-2-((3,4-dihydroxy-phenethyl)amino)-2-oxoethyl 3,7-dimethylocta-2,6-dienoate;
(E)-2-((4,5-dihydroxy-2-iodophenethyl)amino)-2-oxoethyl 3,7-dimethylocta-2,6-dienoate;
(4E,8E,12E,16E)-2-((3,4-dihydroxyphenethyl)amino)-2-oxoethyl 4,8,13,17,21-pentamethyldocosa-4,8,12,16,20-pentaenoate;
(4E,8E,12E,16E)-2-((4,5-dihydroxy-2-iodophenethyl)-amino)-2-oxoethyl 4,8,13,17,21-pentamethyl-docosa-4,8,12,16,20-pentaenoate;
2-((3,4-dihydroxyphenethyl)-amino)-2-oxoethyl oleate;
2-((4,5-dihydroxy-2-iodophenethyl)amino)-2-oxoethyl oleate;
(5Z,8Z,11Z,14Z)-2-((3,4-dihydroxyphenethyl)amino)-2-oxoethyl icosa-5,8,11,14-tetraenoate; and
(5Z,8Z,11Z,14Z)-2-((4,5-dihydroxy-2-iodophenethyl)-amino)-2-oxoethyl icosa-5,8,11,14-tetraenoate.

12. A process for the preparation of a compound of formula (I) as defined in claim 1, which comprises:
a) reacting a compound of formula (II) with a compound of formula (III)

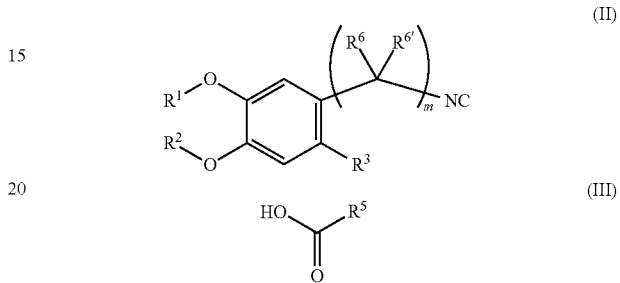

wherein $R^1$, $R^2$, $R^3$, $R^5$, $R^6$, $R^{6'}$ and m are as defined in claim 1; in the presence of formaldehyde to yield a compound of formula (I);
b) optionally converting, in one or a plurality of steps, the compound of formula (I) thus obtained into another compound of formula (I); and
c) optionally reacting the compound of formula (I) obtained in any of the steps a) or b) with a base or with an acid to give the corresponding salt.

13. A pharmaceutical, veterinary or cosmetic composition which comprises an effective amount of a compound of formula (I) as defined in claim 1, together with one or more pharmaceutically or veterinary acceptable excipients or carriers.

14. A method for the treatment and/or prevention of conditions or diseases mediated by the inhibition of TRPV1, comprising administering an effective amount of the compound of formula (I) as defined in claim 1, and one or more pharmaceutically, veterinary or cosmetically acceptable excipients or carriers, in a subject in need thereof, wherein the condition and/or disease mediated by the inhibition of TRPV1 is selected from pain, inflammation, cancer, sensitive skin, itch (pruritus), rosacea, acne vulgaris, atopic dermatitis, psoriasis and psoriatic arthritis.

15. The compound of formula (I) according to claim 1, wherein $R^1$, $R^2$, $R^3$, $R^6$, $R^{6'}$ and m are as defined in claim 1, and $R^5$ is selected from the group consisting of ($C_3$-$C_{28}$)alkyl and unsaturated ($C_3$-$C_{28}$)hydrocarbon, wherein ($C_3$-$C_{28}$)alkyl and unsaturated ($C_3$-$C_{28}$)hydrocarbon are optionally substituted with one or more substituents selected from the group consisting of halogen, —COOH, —OH, —NH$_2$, —COOR$_6$, —NO$_2$, —CF$_3$, —OCF$_3$, —CN, —OR$_6$, —CONH$_2$, —CONHR$_6$, —NHR$_6$, —NHCOR$_6$, —NHSO$_2$R$_6$, and —SO$_2$NHR$_6$.

16. The compound of claim 1, wherein the compound of formula (I) is selected from the group consisting of:
(Z)-2-((4-hydroxy-3-methoxy-benzyl)amino)-2-oxoethyl 12-(2-phenylacetoxy)octadec-9-enoate, and
(Z)-2-((4-hydroxy-2-iodo-5-methoxybenzyl)amino)-2-oxoethyl 12-(2-phenyl-acetoxy)octadec-9-enoate.

* * * * *